United States Patent
Burnette et al.

(10) Patent No.: US 11,278,244 B2
(45) Date of Patent: Mar. 22, 2022

(54) SYSTEMS, DEVICES AND METHODS FOR ANALYTE MONITORING SYSTEM

(71) Applicant: DexCom, Inc., San Diego, CA (US)

(72) Inventors: Douglas William Burnette, San Diego, CA (US); Hari Hampapuram, Carlsbad, CA (US); Apurv Ullas Kamath, San Diego, CA (US); Shawn Larvenz, Ramona, CA (US); Aditya Mandapaka, San Diego, CA (US); Zebediah L. McDaniel, San Diego, CA (US); Tom Miller, Jonestown, TX (US); Jeffrey R. Wedekind, San Diego, CA (US); Yonghuang Zeng, San Diego, CA (US); Stephen Alan Reichert, San Diego, CA (US)

(73) Assignee: Dexcom, Inc., San Diego, CA (US)

(*) Notice: Subject to any disclaimer, the term of this patent is extended or adjusted under 35 U.S.C. 154(b) by 380 days.

(21) Appl. No.: 15/462,239

(22) Filed: Mar. 17, 2017

(65) Prior Publication Data

US 2017/0281092 A1  Oct. 5, 2017

Related U.S. Application Data

(60) Provisional application No. 62/315,539, filed on Mar. 30, 2016.

(51) Int. Cl.
*A61B 5/00* (2006.01)
*A61B 5/1473* (2006.01)
(Continued)

(52) U.S. Cl.
CPC .......... *A61B 5/7203* (2013.01); *A61B 5/1473* (2013.01); *A61B 5/14532* (2013.01);
(Continued)

(58) Field of Classification Search
CPC . A61B 5/7203; A61B 5/14532; A61B 5/1473; A61B 5/14546; A61B 5/1459;
(Continued)

(56) References Cited

U.S. PATENT DOCUMENTS

| | | | |
|---|---|---|---|
| 5,863,401 A | * | 1/1999 | Chen ................ G01N 27/44726 204/451 |
| 6,001,067 A | | 12/1999 | Shults et al. |

(Continued)

FOREIGN PATENT DOCUMENTS

| CN | 1192273 A | 9/1998 |
|---|---|---|
| CN | 101500481 A | 8/2009 |

(Continued)

OTHER PUBLICATIONS

Extended European Search Report for Application No. 17776303.4 dated Oct. 17, 2019, 12 pages.

(Continued)

*Primary Examiner* — Allen Porter
*Assistant Examiner* — Avery M Foley
(74) *Attorney, Agent, or Firm* — Patterson + Sheridan, LLP

(57) ABSTRACT

Systems and methods are provided for detecting changes or fluctuations in an analyte concentration signal that are abnormal, e.g., exceed a predetermined threshold, current trend of analyte concentration measurements, etc. Signals indicative of an analyte concentration in a host may be received from an analyte sensor. The signals may be monitored, and a determination can be made as to whether there is a change in the signal. Upon detecting such a change, the change can be compensated for such that a representation of the signal indicates the analyte concentration. Optionally, the cause of the detected changes or fluctuations can also be determined and information regarding the detected changes (Continued)

or fluctuations can be recorded and analyzed for subsequent optimization of the systems and methods as well for transmitting alerts, notifications, etc. to a user to take corrective action.

8 Claims, 18 Drawing Sheets

(51) Int. Cl.
 *A61B 5/145* (2006.01)
 *A61B 5/1486* (2006.01)
 *A61B 5/1459* (2006.01)
(52) U.S. Cl.
 CPC ........ *A61B 5/14865* (2013.01); *A61B 5/7225* (2013.01); *A61B 5/7445* (2013.01); *A61B 5/1459* (2013.01); *A61B 5/14546* (2013.01); *A61B 5/7221* (2013.01); *A61B 5/7275* (2013.01); *A61B 2562/0219* (2013.01); *A61B 2562/0247* (2013.01); *A61B 2562/0271* (2013.01)
(58) Field of Classification Search
 CPC ... A61B 5/7221; A61B 5/7275; A61B 5/7445; A61B 5/7225; A61B 5/14865; A61B 2562/0271; A61B 2562/0247; A61B 2562/0219
 See application file for complete search history.

(56) References Cited

U.S. PATENT DOCUMENTS

| | | | |
|---|---|---|---|
| 6,233,471 B1 | 5/2001 | Berner et al. | |
| 6,353,324 B1 | 3/2002 | Uber et al. | |
| 6,424,847 B1 | 6/2002 | Mastrototaro et al. | |
| 6,477,395 B2 | 11/2002 | Schulman et al. | |
| 6,484,046 B1 | 11/2002 | Say et al. | |
| 6,512,939 B1 | 1/2003 | Colvin et al. | |
| 6,565,509 B1 | 5/2003 | Say et al. | |
| 6,579,690 B1 | 6/2003 | Bonnecaze et al. | |
| 6,931,327 B2 | 8/2005 | Goode et al. | |
| 7,081,195 B2 | 7/2006 | Simpson et al. | |
| 7,310,544 B2 | 12/2007 | Brister et al. | |
| 7,918,801 B2 | 4/2011 | Cochran | |
| 9,936,903 B2 | 4/2018 | Gofman et al. | |
| 2001/0002206 A1 | 5/2001 | Diab et al. | |
| 2005/0003598 A1 | 1/2005 | Wang et al. | |
| 2005/0027463 A1 | 2/2005 | Goode et al. | |
| 2005/0043598 A1 | 2/2005 | Goode et al. | |
| 2005/0143635 A1 | 6/2005 | Kamath et al. | |
| 2005/0154271 A1 | 7/2005 | Rasdal et al. | |
| 2005/0192557 A1 | 9/2005 | Brauker et al. | |
| 2005/0203360 A1 | 9/2005 | Brauker et al. | |
| 2006/0020187 A1 | 1/2006 | Brister et al. | |
| 2006/0222566 A1 | 10/2006 | Brauker et al. | |
| 2006/0265022 A1* | 11/2006 | John | A61B 5/14553 607/45 |
| 2007/0016381 A1 | 1/2007 | Kamath et al. | |
| 2007/0027385 A1 | 2/2007 | Brister et al. | |
| 2007/0032706 A1 | 2/2007 | Kamath et al. | |
| 2007/0055117 A1* | 3/2007 | Alphonse | A61B 5/14558 600/310 |
| 2007/0197890 A1 | 8/2007 | Boock et al. | |
| 2007/0203966 A1 | 8/2007 | Brauker et al. | |
| 2007/0208245 A1 | 9/2007 | Brauker et al. | |
| 2007/0213611 A1 | 9/2007 | Simpson et al. | |
| 2008/0033254 A1 | 2/2008 | Kamath et al. | |
| 2008/0083617 A1 | 4/2008 | Simpson et al. | |
| 2008/0119703 A1 | 5/2008 | Brister et al. | |
| 2009/0192751 A1 | 7/2009 | Kamath et al. | |
| 2012/0262298 A1* | 10/2012 | Bohm | A61B 5/1495 340/604 |
| 2013/0018597 A1 | 1/2013 | Gofman et al. | |
| 2013/0237774 A1* | 9/2013 | Schentag | A61B 1/00009 600/301 |
| 2014/0114156 A1 | 4/2014 | Bohm et al. | |
| 2014/0180049 A1 | 6/2014 | Brauker et al. | |
| 2015/0164371 A1 | 6/2015 | Varsavsky et al. | |
| 2017/0181677 A1* | 6/2017 | Varsavsky | A61B 5/14532 |
| 2017/0319112 A1* | 11/2017 | Schmelzeisen-Redeker | A61M 5/1723 |

FOREIGN PATENT DOCUMENTS

| | | |
|---|---|---|
| CN | 104736057 A | 6/2015 |
| JP | 2002514452 A | 5/2002 |
| JP | 2002529742 A | 9/2002 |
| JP | 2007533346 A | 11/2007 |
| JP | 2015527093 A | 9/2015 |
| JP | 2016502420 A | 1/2016 |
| WO | WO 2005/018443 | 3/2005 |
| WO | WO 2013/184416 | 12/2013 |

OTHER PUBLICATIONS

International Preliminary Report on Patentability for Application No. PCT/US2017/023081 dated Oct. 11, 2018, 12 pages.
International Search Report and Written Opinion for Application No. PCT/US2017/023081 dated Jul. 11, 2017, 14 pages.
Office Action for Chinese Application No. 201780016967.0, dated Dec. 31, 2020, 21 pages.
Office Action for Japanese Application No. 2018-545895, dated Mar. 1, 2021, 14 pages.
Office Action from Canadian Patent Application No. 3,014,678, dated Mar. 29, 2021, 4 pages.

* cited by examiner

SYSTEMS, DEVICES AND METHODS FOR ANALYTE MONITORING SYSTEM

INCORPORATION BY REFERENCE TO RELATED APPLICATION

Any and all priority claims identified in the Application Data Sheet, or any correction thereto, are hereby incorporated by reference under 37 CFR 1.57. This application claims the benefit of U.S. Provisional Application No. 62/315,539, filed on Mar. 30, 2016. The aforementioned application is incorporated by reference herein in its entirety, and is hereby expressly made a part of this specification.

FIELD

Various embodiments relate generally to continuous monitoring of analyte values received from an analyte sensor system, and in particular, to transmitter fault detection and responses to such faults.

BACKGROUND

Diabetes mellitus is a disorder in which the pancreas cannot create sufficient insulin (Type I or insulin dependent) and/or in which insulin is not effective (Type 2 or non-insulin dependent). In the diabetic state, the victim suffers from high blood sugar, which causes an array of physiological derangements (kidney failure, skin ulcers, or bleeding into the vitreous of the eye) associated with the deterioration of small blood vessels. A hypoglycemic reaction (low blood sugar) may be induced by an inadvertent overdose of insulin, or after a normal dose of insulin or glucose-lowering agent accompanied by extraordinary exercise or insufficient food intake.

Conventionally, a diabetic person carries a self-monitoring blood glucose (SMBG) monitor, which typically requires uncomfortable finger pricking methods. Due to the lack of comfort and convenience, a diabetic person will normally only measure his or her glucose level two to four times per day. Unfortunately, these time intervals are spread so far apart that the diabetic person will likely find out too late, sometimes incurring dangerous side effects, of a hyperglycemic or hypoglycemic condition. In fact, it is not only unlikely that a diabetic person will take a timely SMBG value, but it is also unlikely that the diabetic will know if his or her blood glucose value is going up (higher) or down (lower) utilizing conventional monitoring systems and methods.

Consequently, a variety of non-invasive, transdermal (e.g., transcutaneous) and/or implantable electrochemical sensors are being developed for continuously detecting and/or quantifying blood glucose values. These devices generally transmit raw or minimally processed data for subsequent analysis at a remote device, which can include a display.

SUMMARY

Details of one or more implementations of the subject matter described in this specification are set forth in the accompanying drawings and the description below. Other features, aspects, and advantages will become apparent from the description, the drawings, and the claims. Note that the relative dimensions of the following figures may not be drawn to scale.

In accordance with one embodiment, a computer-implemented method, comprises receiving a signal indicative of an analyte concentration in a host from an analyte sensor, and monitoring the signal. The computer-implemented method further comprises determining whether there is a change in the signal, and compensating for the change in the signal such that a representation of the signal reflects the analyte concentration in the host.

In accordance with one embodiment, a method comprises comparing a current clock time to a previously stored clock time after experiencing a disruption in operation of sensor measurement circuitry in an analyte sensor system. The method further comprises synchronizing the current clock time to the previously stored clock time, and incrementing a timestamp associated with EGV data transmissions based upon the previously stored clock time.

In accordance with one embodiment, a system comprises an analyte sensor adapted to transmit analyte concentration data. The system further comprises sensor measurement circuitry adapted to receive analyte concentration data from the sensor and detect a change in the analyte concentration data, wherein the sensor measurement circuitry compensates for a fluctuation exceeding a predetermined threshold in the analyte concentration data.

In accordance with one embodiment, sensor electronics, comprises a processor, and an offset circuit. The offset circuit is configured to apply an offset current to a received analyte concentration signal affected by noise upon a determination by the processor of the existence of the noise.

In accordance with one embodiment, a method, comprises receiving one or more operating parameters associated with a battery at a processor of a system operating under power provided by the battery. The method further comprises monitoring performance characteristics of the battery, and determining whether the monitored performance characteristics deviate from reference performance characteristics based upon the one or more received operating parameters. Further still, the method comprises wirelessly updating the one or more operating parameters upon a determination that the monitored performance characteristics deviate from the reference performance characteristics.

In accordance with one embodiment, a method, comprises receiving one or more operating parameters indicative of a battery profile at a processor controlling sensor measurement circuitry. The method further comprises receiving bounds input based upon the one or more operating parameters and determining whether the one or more received operating parameters falls within the received bounds input. Further still, the method comprises sending a notification to a user interface associated with the sensor measurement circuitry that the one or more operating parameters require updating upon a determination that the one or more received operating parameters fall outside of the received bounds input.

In accordance with one embodiment, a method comprises determining a schedule information of an operation of an analyte sensor system and identifying a payload information associated with the operation. The method further comprises calculating an operational frequency of a charge pump according to the payload and schedule information. Further still, the method comprises instructing the charge pump to operate at the calculated operational frequency during an occurrence of the operation.

Any of the features of aspects specified herein are applicable to all other aspects and embodiments identified herein. Moreover, any of the features of an aspect is independently combinable, partly or wholly with other aspects described herein in any way, e.g., one, two, or three or more aspects may be combinable in whole or in part. Further, any of the features of an aspect may be made optional to other aspects. Any aspect of a method can be performed by a system or apparatus of another aspect, and any aspect or of a system can be configured to perform a method of another aspect.

BRIEF DESCRIPTION OF THE DRAWINGS

Various embodiments are described in detail with reference to the accompanying figures. The drawings are provided for purposes of illustration only and merely depict typical or example embodiments. These drawings are provided to facilitate the reader's understanding of the systems and methods described herein, and shall not be considered limiting of the breadth, scope, or applicability of the various embodiments.

DETAILED DESCRIPTION

Figure 1:
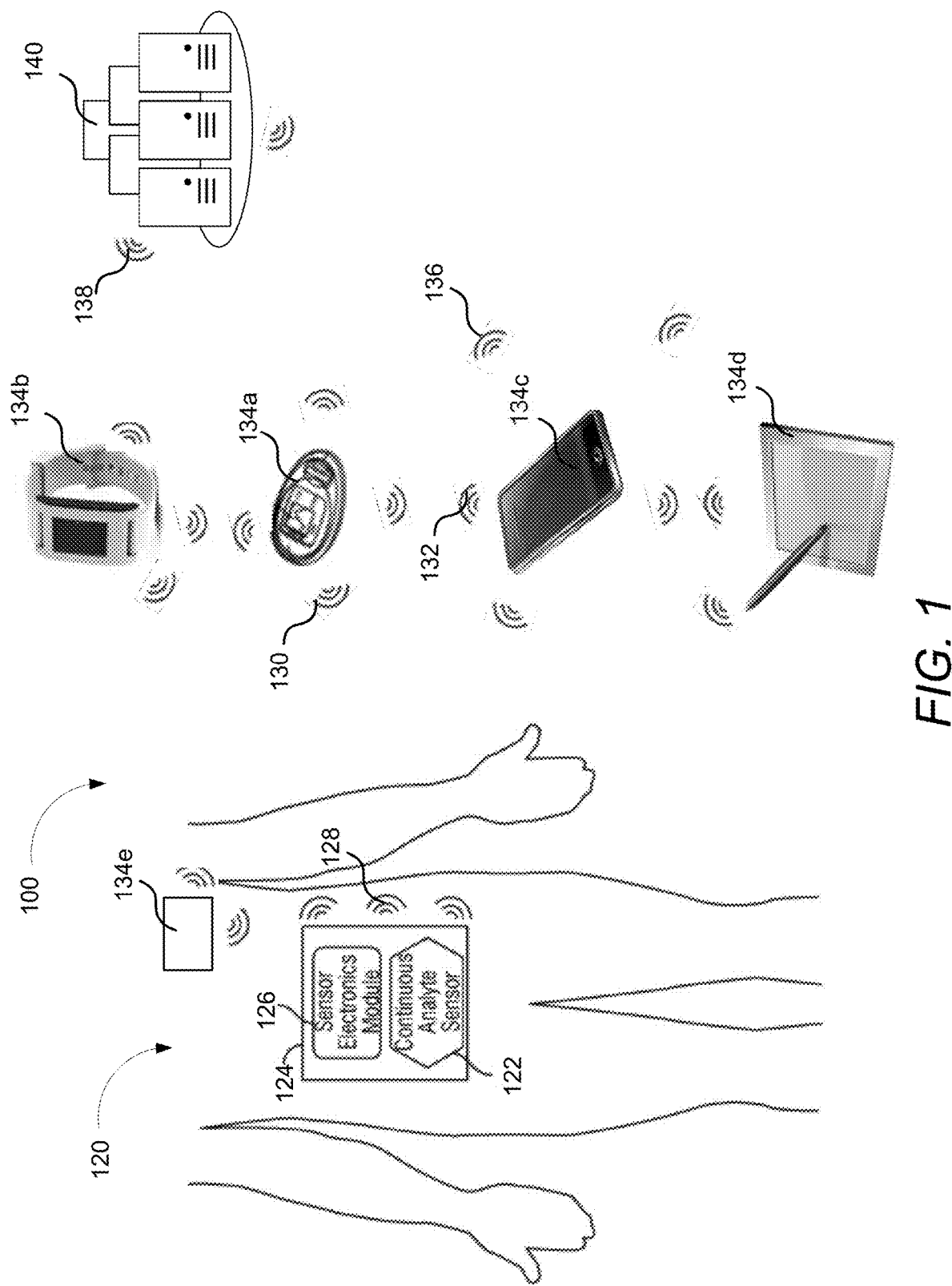
FIG. 1 is a diagram illustrating certain embodiments of an example continuous analyte sensor system communicating with at least one display device in accordance with various technologies described in the present disclosure.

The following description illustrates some example embodiments of the disclosed technology(ies) in detail. Those of skill in the art will recognize that there are numerous variations and modifications of the disclosed embodiments that are encompassed by its scope. Accordingly, the description of a certain example embodiment should not be deemed to limit the scope of the present disclosure.

Overview

The aforementioned continuous detection and/or quantification of blood glucose values can be accomplished using a continuous glucose monitor (CGM), one example of a continuous analyte sensor. In particular, the continuous analyte sensor measures the concentration of a given analyte within the host, e.g., glucose, and a raw signal is generated by electronics (sometimes referred to as a sensor electronics module) associated with the continuous analyte sensor. The sensor electronics module can be physically connected to the continuous analyte sensor and includes electronics/sensor measurement circuitry configured to process a data stream associated with the analyte concentration measured by the continuous analyte sensor in order to generate sensor information that includes the raw signal/raw sensor data, transformed sensor data, and/or any other sensor data or data derived therefrom, e.g., predictive or trend data. The sensor electronics module may further be configured to generate sensor information that is customized for respective display devices, such that different display devices may receive different sensor information for presentation to the host, a host care taker, etc. Further still, the sensor electronics module includes one or more communication modules, such as wireless radio transmitters for transmitting the sensor information to the display devices. The display devices may include one or more communication modules for transmitting sensor information or other data, such as fault or error information (described in greater detail below) to a remote server or database.

The above discussion assumes a reliable and true raw signal is received by the sensor electronics module. However, in some cases, faults or errors may occur and the raw signal is no longer reliable and true. These faults or errors may be detectable by analysis of the signal, analysis of the clinical context, or both. Discrimination can therefore be performed to distinguish the same from actual measured signal behavior, as well as for responsive signal processing, which can vary according to the fault. Accordingly, appropriate fault discrimination and responsive processing techniques are employed.

Faults or errors may be caused in a number of ways, whether they're associated with a physiological activity in the host, e.g., metabolic responses, and/or associated with an in vivo portion of the continuous analyte sensor as the same settles into the host environment, during use over time, etc. They may also be associated with transient events within the control of a patient or with the external environment surrounding continuous analyte sensor. Accordingly, various embodiments are directed to fault or error detection in a continuous analyte sensor system, and the implementation of one or more corrective/compensatory actions in response to the detected fault or error so that a user of the analyte sensor system is provided with accurate analyte measurement data. For example, in accordance with various embodiments, an anomalous or abnormal change or fluctuation in a signal indicative of an analyte concentration in a host can be detected. Once detected, the cause(s) of the change in the signal can be determined, and the change in the signal can be accounted for such that the analyte concentration is the host is represented accurately.

The term "analyte" as used herein is a broad term and is to be given its ordinary and customary meaning to a person of ordinary skill in the art (and is not to be limited to a special or customized meaning), and furthermore refers without limitation to a substance or chemical constituent in a biological fluid (for example, blood, interstitial fluid, cerebral spinal fluid, lymph fluid or urine) that can be analyzed. Analytes can include naturally occurring substances, artificial substances, metabolites, and/or reaction products. In some embodiments, the analyte for measurement by the sensor heads, devices, and methods is analyte. However, other analytes are contemplated as well, including but not limited to acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-β hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, analyte-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, Plasmodium vivax, sexual differentiation, 21-deoxycortisol); desbutylhalofantrine; dihydropteridine reductase; diptheri/tetanus antitoxin; erythrocyte arginase; erythrocyte protoporphyrin; esterase D; fatty acids/acylglycines; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; analyte-6-phosphate dehydrogenase; glutathione; glutathione peroxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A-1, β); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis, Echinococcus granulosus, Entamoeba histolytica*, enterovirus, *Giardia duodenalisa, Helicobacter pylori*, hepatitis B virus, herpes virus, HIV-1, IgE (atopic disease), influenza virus, *Leishmania donovani*, leptospira, measles/mumps/rubella, *Mycobacterium leprae, Mycoplasma pneumoniae*, Myoglobin, *Onchocerca volvulus*, parainfluenza virus, *Plasmodium falciparum*, poliovirus, *Pseudomonas aeruginosa*, respiratory syncytial virus, rickettsia (scrub typhus), *Schistosoma mansoni, Toxoplasma gondii, Trepenoma pallidium, Trypanosoma cruzi/rangeli*, vesicular stomatis virus, *Wuchereria bancrofti*, yellow fever virus); specific antigens (hepatitis B virus, HIV-1); succinylacetone; sulfadoxine; theophylline; thyrotropin (TSH); thyroxine (T4); thyroxine-binding globulin; trace elements; transferring; UDP-galactose-4-epimerase; urea; uroporphyrinogen I synthase; vitamin A; white blood cells; and zinc protoporphyrin. Salts, sugar, protein, fat, vitamins, and hormones naturally occurring in blood or interstitial fluids can also constitute analytes in certain embodiments. The analyte can be naturally present in the biological fluid, for example, a metabolic product, a hormone, an antigen, an antibody, and the like. Alternatively, the analyte can be introduced into the body, for example, a contrast agent for imaging, a radioisotope, a chemical agent, a fluorocarbon-based synthetic blood, or a drug or pharmaceutical composition, including but not limited to insulin; ethanol; cannabis (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbiturates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-Dihydroxyphenylacetic acid (DOPAC), Homovanillic acid (HVA), 5-Hydroxytryptamine (5HT), and 5-Hydroxyindoleacetic acid (FHIAA).

In some embodiments, a system is provided for continuous measurement of an analyte in a host that includes: a continuous analyte sensor configured to continuously measure a concentration of the analyte in the host; and a sensor electronics module physically connected to the continuous analyte sensor to receive the analyte concentration measurements and communicate them to display devices. In particular, the sensor electronics module includes electronics configured to process a data stream associated with an analyte concentration measured by the continuous analyte sensor in order to generate sensor information that includes raw sensor data, transformed sensor data, and/or any other sensor data or data derived therefrom, e.g., predictive or trend data. The sensor electronics module may further be configured to generate sensor information that is customized for respective display devices, such that different display devices may receive different sensor information for presentation to the host, a host care taker, etc. Further still, the sensor electronics module includes one or more communication modules, such as wireless radio transmitters for transmitting the sensor information to the display devices.

The terms "raw data," "raw data stream", "raw data signal", "data signal", and "data stream" as used herein can refer without limitation to an analog or digital signal from the continuous analyte sensor related to a measured analyte. For example, a raw data stream provided by the continuous analyte sensor to the sensor electronics module may be digital data in "counts" converted by an A/D converter from an analog signal (for example, voltage or current) representative of an analyte concentration, which can include a plurality of time spaced data points from a substantially continuous analyte sensor, each of which comprises individual measurements taken at time intervals ranging from fractions of a second up to, for example, one, two, or five minutes or longer. In some embodiments, the raw data/counts may be representative of sensor information that has been integrated or averaged over a time period (e.g., five minutes). Moreover, the term "count" can refer to a unit of measurement of a digital signal. For example, a raw data stream or raw data signal measured in counts is related to a voltage (for example, converted by an A/D converter), which is directly related to current from a working electrode (described in greater detail below).

In some embodiments, the sensor electronics module may be configured to search for and/or attempt to wirelessly communicate with a display device. In some embodiments, the search for and/or attempted wireless communication with the display device can occur in a predetermined and/or programmable order (e.g., grading and/or escalating). It should be noted that the sensor electronics module is not necessarily tied to a single display device. Rather the sensor electronics module is configured to communicate with a plurality of different display devices directly, systematically, simultaneously (e.g., via broadcasting), regularly, periodically, randomly, on-demand, in response to a query, based on alerts or alarms, and/or the like.

Depending on the embodiment, the sensor electronics module receives sensor information from the continuous analyte sensor. This sensor information may be raw data which the display device receives and processes, e.g., in accordance with one or more algorithms, for generating and/or displaying estimated analyte values. In the context of continuous glucose monitoring, the estimated analyte values may be estimated glucose value (EGV) data. For example, some display devices may comprise software including display instructions (software programming comprising instructions configured to display the sensor information and optionally query the sensor electronics module to obtain the displayable sensor information) configured to enable display of the displayable sensor information thereon.

In other embodiments, the processing of the raw data may be performed at the sensor electronics module. That is, the requisite algorithms, software, and/or other processing functionality for transforming the raw data into estimated analyte value data may be implemented at the sensor electronics module rather than at the display device. Transforming the raw data at the sensor electronics module may avoid the possibility for inconsistent estimated analyte value data, e.g., due to inconsistent calibration between two or more display devices. Moreover, implementing this functionality at the sensor electronics module may discourage third party display device/medicament delivery device providers from tampering or otherwise altering the processing algorithms and software.

In some embodiments, certain display devices may be in direct wireless communication with the sensor electronics module, although intermediate network hardware, firmware, and/or software can be included within the direct wireless communication. In some embodiments, a repeater (e.g., a Bluetooth repeater) can be used to re-transmit the transmitted sensor information to a location farther away than the immediate range of the telemetry module of the sensor electronics module. In some embodiments, a receiver (e.g., Bluetooth receiver) can be used to re-transmit the transmitted sensor information to a display device, e.g., a TV screen, possibly in a different format, such as in a text message.

In some embodiments, one or more display devices are configured to query the sensor electronics module for sensor information, where the display device requests sensor information from the sensor electronics module in an "on-demand" fashion, for example, in response to a query. In some embodiments, the sensor electronics module is configured for periodic, systematic, regular, or irregular or aperiodic transmission of sensor information to one or more display devices (for example, every one, two, five, or ten minutes or more). In some embodiments, the sensor electronics module is configured to transmit data packages associated with a triggered alert (e.g., triggered by one or more alert conditions). However, any combination of the above described statuses of data transmission can be implemented with any combination of a paired sensor electronics module and display device(s).

Example Configurations of a Continuous Analyte Monitoring System

An analyte sensor, such as a glucose sensor can be any device capable of measuring the concentration of an analyte. One exemplary embodiment is described below, which utilizes an implantable glucose sensor. However, it should be understood that the devices and methods described herein can be applied to any device capable of detecting a concentration of glucose or a substance indicative of the concentration or presence of another analyte and providing an output signal that represents the concentration of glucose.

In some embodiments, the glucose sensor is a continuous device, for example a subcutaneous, transdermal, transcutaneous, non-invasive, intraocular and/or intravascular (e.g., intravenous) device. In some embodiments, a plurality of intermittent blood samples can be analyzed. The glucose sensor can use any method of glucose measurement, including enzymatic, chemical, physical, electrochemical, optical, optochemical, fluorescence-based, spectrophotometric, spectroscopic (e.g., optical absorption spectroscopy, Raman spectroscopy, etc.), polarimetric, calorimetric, iontophoretic, radiometric, and the like.

The glucose sensor can use any known detection method, including invasive, minimally invasive, and non-invasive sensing techniques, to provide a data stream indicative of the concentration of the analyte in a host. The data stream, as discussed above, is typically a raw data signal that is used to provide a useful value of the analyte to a user, such as a patient or health care professional (e.g., doctor), who may be using the sensor.

In one preferred embodiment, the analyte sensor is an implantable glucose sensor, such as described with reference to U.S. Pat. No. 6,001,067 and U.S. Patent Publication No. 2005/0027463. In another preferred embodiment, the analyte sensor is a transcutaneous glucose sensor, such as described with reference to U.S. Patent Publication No. 2006/0020187. In still other embodiments, the sensor is configured to be implanted in a host vessel or extracorporeally, such as is described in U.S. Patent Publication No. 2007/0027385, U.S. Patent Publication No. 2008/0119703, U.S. Patent Publication No. 2008/0108942, and U.S. Patent Publication No. 2007/0197890. In one alternative embodiment, the continuous glucose sensor comprises a transcutaneous sensor such as described in U.S. Pat. No. 6,565,509 for example. In another alternative embodiment, the continuous glucose sensor comprises a subcutaneous sensor such as described with reference to U.S. Pat. Nos. 6,579,690 or 6,484,046, for example. In another alternative embodiment, the continuous glucose sensor comprises a refillable subcutaneous sensor such as described with reference to U.S. Pat. No. 6,512,939, for example. In another alternative embodiment, the continuous glucose sensor comprises an intravascular sensor such as described with reference to U.S. Pat. No. 6,477,395, for example. In another alternative embodiment, the continuous glucose sensor comprises an intravascular sensor such as described with reference to U.S. Pat. No. 6,424,847.

FIG. 1 is a diagram depicting an example continuous analyte monitoring system 100 including an analyte sensor system 124 operatively connected to a host 120 and a plurality of display devices 134a-e according to certain aspects of the present disclosure. It should be noted that display device 134e alternatively or in addition to being a display device, may be a medicament delivery device that can act cooperatively with the analyte sensor system 124 to deliver medicaments to host 120. The analyte sensor system 124 may include a sensor electronics module 126 and a continuous analyte sensor 122 associated with the sensor electronics module 126. The sensor electronics module 126 may be in direct wireless communication with one or more of the plurality of the display devices 134a-e via wireless communications signals. As will be discussed in greater detail below, display devices 134a-e may also communicate amongst each other and/or through each other to analyte sensor system 124. For ease of reference, wireless communications signals from analyte sensor system 124 to display devices 134a-e can be referred to as "uplink" signals 128. Wireless communications signals from, e.g., display devices 134a-e to analyte sensor system 124 can be referred to as "downlink" signals 130. Wireless communication signals between two or more of display devices 134a-e may be referred to as "crosslink" signals 132. Additionally, wireless communication signals can include data transmitted by one or more of display devices 134a-d via "long-range" uplink signals 136 (e.g., cellular signals) to one or more remote servers 140 or network entities, such as cloud-based servers or databases, and receive long-range downlink signals 138 transmitted by remote servers 140.

The sensor electronics module 126 includes sensor electronics that are configured to process sensor information and generate transformed sensor information. In certain embodiments, the sensor electronics module 126 includes electronic circuitry associated with measuring and processing data from continuous analyte sensor 122, including prospective algorithms associated with processing and calibration of the continuous analyte sensor data. The sensor electronics module 126 can be integral with (non-releasably attached to) or releasably attachable to the continuous analyte sensor 122 achieving a physical connection therebetween. The sensor electronics module 126 may include hardware, firmware, and/or software that enables analyte level measurement. For example, the sensor electronics module 126 can include a potentiostat, a power source for providing power to continuous analyte sensor 122, other components useful for signal processing and data storage, and a telemetry module for transmitting data from itself to one or more display devices 134a-e. Electronics can be affixed to a printed circuit board (PCB), or the like, and can take a variety of forms. For example, the electronics can take the form of an integrated circuit (IC), such as an Application-Specific Integrated Circuit (ASIC), a microcontroller, and/or a processor. Examples of systems and methods for processing sensor analyte data are described in more detail herein and in U.S. Pat. Nos. 7,310,544 and 6,931,327 and U.S. Patent Publication Nos. 2005/0043598, 2007/0032706, 2007/0016381, 2008/0033254, 2005/0203360, 2005/0154271, 2005/0192557, 2006/0222566, 2007/0203966 and 2007/0208245, all of which are incorporated herein by reference in their entirety for all purposes.

Display devices 134a-e are configured for displaying, alarming, and/or basing medicament delivery on the sensor information that has been transmitted by the sensor electronics module 126 (e.g., in a customized data package that is transmitted to one or more of display devices 134a-e based on their respective preferences). Each of the display devices 134a-e can include a display such as a touchscreen display for displaying sensor information to a user (most often host 120 or a care taker/medical professional) and/or receiving inputs from the user. In some embodiments, the display devices 134a-e may include other types of user interfaces such as a voice user interface instead of or in addition to a touchscreen display for communicating sensor information to the user of the display device 134a-e and/or receiving user inputs. In some embodiments, one, some or all of the display devices 134a-e are configured to display or otherwise communicate the sensor information as it is communicated from the sensor electronics module 126 (e.g., in a data package that is transmitted to respective display devices 134a-e), without any additional prospective processing required for calibration and real-time display of the sensor information.

In the embodiment of FIG. 1, one of the plurality of display devices 134a-e may be a custom display device 134a specially designed for displaying certain types of displayable sensor information associated with analyte values received from the sensor electronics module 126 (e.g., a numerical value and an arrow, in some embodiments). In some embodiments, one of the plurality of display devices 134a-e may be a handheld device 134c, such as a mobile phone based on the Android, iOS operating system or other operating system, a palm-top computer and the like, where handheld device 134c may have a relatively larger display and be configured to display a graphical representation of the continuous sensor data (e.g., including current and historic data). Other display devices can include other handheld devices, such as a tablet 134d, a smart watch 134b, a medicament delivery device 134e, a blood glucose meter, and/or a desktop or laptop computer.

As alluded to above, because the different display devices 134a-e provide different user interfaces, content of the data packages (e.g., amount, format, and/or type of data to be displayed, alarms, and the like) can be customized (e.g., programmed differently by the manufacture and/or by an end user) for each particular display device and/or display device type. Accordingly, in the embodiment of FIG. 1, one or more of display devices 134a-e can be in direct or indirect wireless communication with the sensor electronics module 126 to enable a plurality of different types and/or levels of display and/or functionality associated with the sensor information, which is described in more detail elsewhere herein.

Continuous Analyte Sensor

Generally, continuous analyte sensor 122 may be an implantable analyte (e.g., glucose) sensor that utilizes amperometric electrochemical sensor technology to measure glucose concentration. Electrodes comprising continuous analyte sensor 122 may include a working electrode, a counter electrode, and a reference electrode. In one embodiment, the counter electrode is provided to balance the current generated by the species being measured at the working electrode. In the case of a glucose oxidase based glucose sensor, the species being measured at the working electrode is $H_2O_2$. Glucose oxidase catalyzes the conversion of oxygen and glucose to hydrogen peroxide and gluconate according to the following reaction:

Glucose+$O_2$ Gluconate+$H_2O_2$

The change in $H_2O_2$ can be monitored to determine glucose concentration because for each glucose molecule metabolized, there is a proportional change in the product $H_2O_2$. Oxidation of $H_2O_2$ by the working electrode is balanced by reduction of ambient oxygen, enzyme generated $H_2O_2$, or other reducible species at the counter electrode. The $H_2O_2$ produced from the glucose oxidase reaction further reacts at the surface of working electrode and produces two protons ($2H^+$), two electrons ($2e$) and one oxygen molecule ($O_2$).

In some alternative embodiments, additional electrodes can be included within the assembly, for example, a three-electrode system (working, reference, and counter electrodes) and an additional working electrode (e.g., an electrode which can be used to generate oxygen, which is configured as a baseline subtracting electrode, or which is configured for measuring additional analytes). U.S. Pat. No. 7,081,195, U.S. Patent Publication No. 2005/0143635 and U.S. Patent Publication No. 2007/0027385, each of which are incorporated herein by reference, describe some systems and methods for implementing and using additional working, counter, and reference electrodes. In some embodiments wherein two or more working electrodes are provided, the second working electrode may be configured to be substantially similar to the first working electrode, but without an enzyme disposed thereon. In this way, the baseline signal can be determined and subtracted from the first signal to generate a difference signal, i.e., a glucose-only signal that is substantially not subject to fluctuations in the baseline or interfering species on the signal, such as described in U.S. Patent Publication No. 2005/0143635, U.S. Patent Publication No. 2007/0027385, and U.S. Patent Publication No. 2007/0213611, and U.S. Patent Publication No. 2008/0083617, which are incorporated herein by reference in their entirety.

Sensor Electronics Module

Figure 2A:
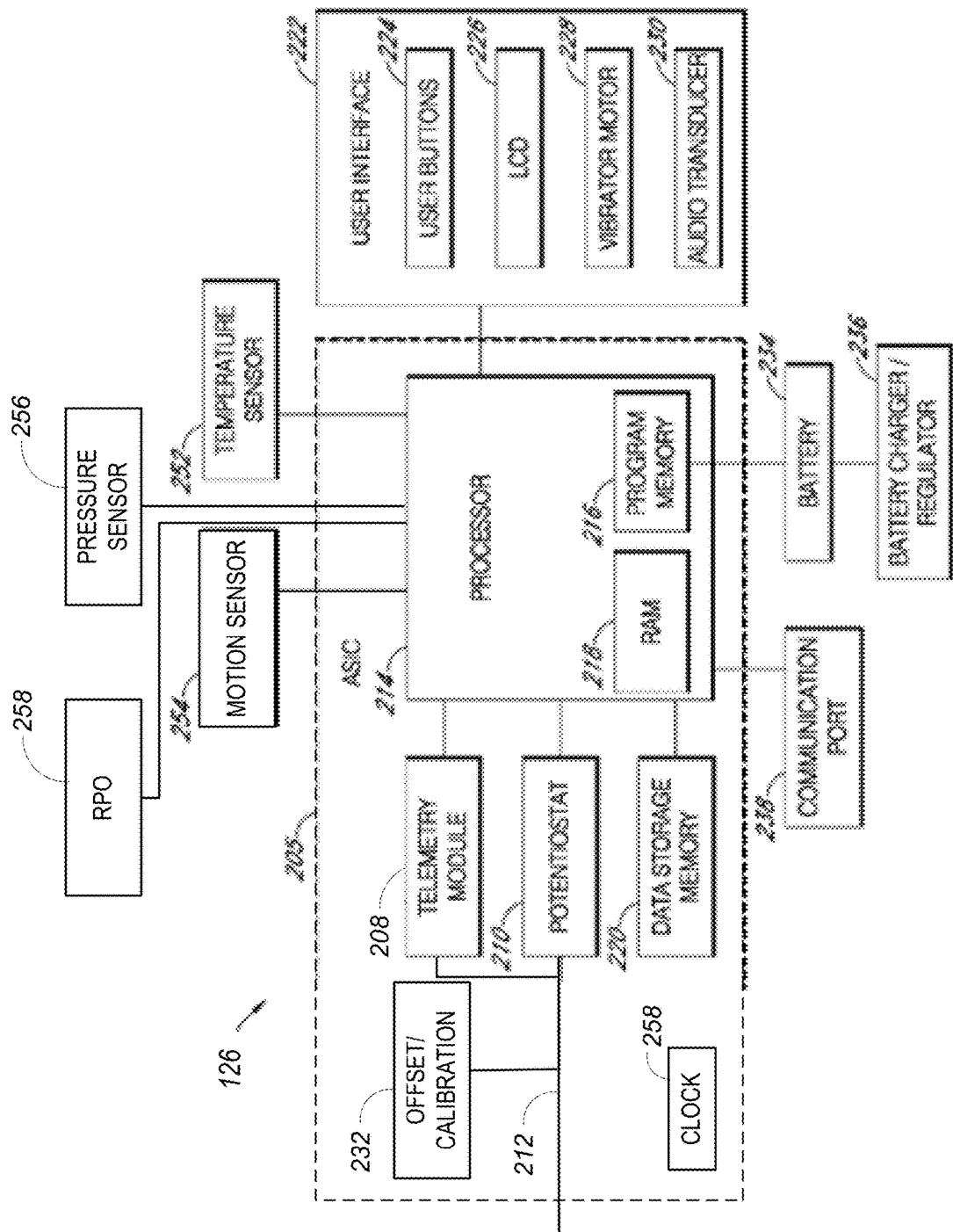
FIG. 2A is a block diagram of an example sensor electronics module of the example continuous analyte sensor system of FIG. 1.

FIG. 2A is a block diagram illustrating embodiments of the sensor electronics module 126 (FIG. 1). The sensor electronics module 12 can include an application-specific integrated circuit (ASIC) 205, a user interface 222, temperature sensor 252, motion sensor 254, body sensor 256, and clock 258. ASIC 205 can also be coupled to a communication port 238 and a battery 234. Although FIG. 2A shows an ASIC 205 that includes much of the electronic circuitry, the ASIC 205 may be replaced with one or more of any suitable logic device, such as field programmable gate arrays (FPGA), microprocessors, analog circuitry, or other digital and/or analog circuitry. Further, ASIC 205 can include one or more additional features of sensor electronics module 126 discussed elsewhere herein, or one or more features illustrated in FIG. 2A as being part of the ASIC—such as telemetry module 208, potentiostat 210, offset/calibration module 232, data storage memory 220, and clock 258-can be separate from the ASIC.

In this embodiment, a potentiostat 210 (one example of an analog front end (AFE)) is coupled to continuous analyte sensor 122 via data line 212, for example, in order to receive sensor information obtained/measured by continuous analyte sensor 122. In some embodiments, the potentiostat 210 provides a voltage to continuous analyte sensor 122 via data line 212 in order to bias continuous analyte sensor 122 to enable measurement of a current value indicative of the analyte concentration in the host (also referred to as the analog portion). The potentiostat 210 can have one channel or multiple channels (and a corresponding one or multiple data lines 212), depending on the number of working electrodes, for example. In some embodiments, the potentiostat 210 includes a resistor (not shown) that translates current into voltage. In some embodiments, a current to frequency converter is provided that is configured to continuously integrate the measured current, for example, using a charge counting device. In some embodiments, an A/D converter digitizes the analog signal into "counts" (previously described) for processing. Accordingly, the resulting raw data stream in counts can be directly related to the current measured by the potentiostat 210.

A processor 214 controls the processing of the sensor electronics module 126. In some embodiments, the processor 214 is formed as part of a custom chip, such as an ASIC, however a computer system other than an ASIC can be used to process data as described herein, for example a microprocessor can be used for some or all of the sensor electronics module processing. Processor 214 typically provides a program memory 216, which provides semi-permanent storage of data, for example, storing data such as sensor identifier (ID) and programming to process data streams (for example, filtering, calibration, fail-safe checking, and the like). Processor 214 can additionally be used for the cache memory of continuous analyte monitoring system 100, for example for temporarily storing recent sensor data. In some embodiments, processor 214 comprises memory storage components such as ROM, RAM, dynamic-RAM, static-RAM, non-static RAM, EEPROM, rewritable ROMs, flash memory, and the like. In one embodiment, RAM 218 can be used for the continuous analyte monitoring system 100's cache memory, for example for temporarily storing recent sensor information.

In some embodiments, processor 214 comprises a digital filter, for example, an infinite or finite impulse response (IIR or FIR) filter, configured to smooth the raw data stream from the A/D converter. Generally, digital filters are programmed to filter data sampled at a predetermined time interval (also referred to as a sample rate). In some embodiments, such as when the potentiostat 210 is configured to measure the analyte at discrete time intervals, these time intervals determine the sample rate of the digital filter. In some alternative embodiments, when potentiostat 210 is configured to continuously measure an analyte, for example, using a current-to-frequency converter, processor 214 can be programmed to request a digital value from an integrator at a predetermined time interval, also referred to as the acquisition time. In these alternative embodiments, the values obtained by the processor 214 can be averaged over the acquisition time due the continuity of the current measurement. Accordingly, the acquisition time determines the sample rate of the digital filter.

In an embodiment, the processor 214 may be further configured to generate data packages for transmission to one or more display devices. Furthermore, processor 214 may generate data packets for transmission to these outside sources, e.g., via telemetry. As discussed above, the data packages may be customizable for each display device 134a-e, for example, and may include any available data, such as sensor information having customized sensor data and/or transformed sensor data, sensor/sensor electronics module ID code, raw data, filtered data, calibrated data, rate of change information, trend information, error detection or correction, and/or the like.

A data storage memory 220 is operably connected to processor 214 and is configured to store a variety of sensor information. In some embodiments, the data storage memory stores, for example, 1, 5, 9, 14, 15, 20, 30 or more days of continuous analyte sensor data. In some embodiments, the data storage memory 220 stores sensor information such as raw sensor data (one or more raw analyte concentration values), calibrated data, filtered data, transformed sensor data, and/or any other displayable sensor information. Although separate data storage memory 220 and program memory 216 are shown in FIG. 2A, one skilled in the art appreciates a variety of configurations, including one or multiple memories that provide the necessary storage space to support sensor electronic module 126 data processing and storage requirements.

A telemetry module 208 is operably connected to the processor module 214 and provides the hardware, firmware, and/or software that enable wireless communication between the sensor electronics module 126 and one or more display devices 134*a-e*. A variety of wireless communication technologies that can be implemented in the telemetry module 208 include radio frequency (RF), infrared (IR), Bluetooth, Bluetooth Low Energy (BLE), spread spectrum communication, frequency hopping communication, ZigBee, IEEE 802.11/802.16, wireless (e.g., cellular) telecommunication, paging network communication, near-field communication (NFC), radio frequency ID (RFID) magnetic induction, satellite data communication, GPRS, ANT, and/or the like. In one preferred embodiment, the telemetry module 208 comprises a Bluetooth chip. In some embodiments, Bluetooth technology is implemented in a combination of the telemetry module 208 and processor 214.

A battery 234 is operatively connected to the processor 214 (and possibly other components of the sensor electronics module 126) and provides the necessary power for the sensor electronics module 126. In some embodiments, the battery is a Lithium Manganese Dioxide battery, however any appropriately sized and powered battery can be used (e.g., AAA, Nickel—cadmium, Zinc—carbon, Alkaline, Lithium, Nickel—metal hydride, Lithium—ion, Zinc—air, Zinc—mercury oxide, Silver-zinc, or hermetically-sealed). In some embodiments battery 234 is rechargeable. In some embodiments, a plurality of batteries can be used to power the system. In some embodiments, battery 234 may be a custom battery having one or more of a customized size, shape, and/or capacity optimized for use in sensor electronics module 126, including reduced capacity in cases where sensor electronics module 126 has lower energy requirements.

It should be noted that flexible electronics or flex circuit technology may be used to attach or incorporate battery 234 to a printed circuit board assembly (PCBA) (on which one or more components of sensor electronics module 126 reside). The use of flex circuit technology negates the conventional need to have battery 234 hard-soldered onto the PCBA allowing battery 234 to be positioned thereon more freely, which in turn allows for more flexibility with regard to the shape of sensor electronics module 126, as well as a reduction in the size of the sensor electronics module 126. Moreover, during conventional installation of a battery on a PCBA, the battery is typically hard-soldered and epoxied onto the PCBA. Because the battery may have different heat characteristics from surrounding circuitry, the heating of the battery due to the epoxy process can cause flexing of the PCBA and/or other components installed thereon. In contrast, use of flex circuit technology allows battery 234 to move during the epoxy hardening process without affecting the surrounding circuitry.

A battery charger and/or regulator 236 may be configured to receive energy from an internal and/or external charger. In some embodiments, a battery regulator (or balancer) 236 regulates the recharging process by bleeding off excess charge current to allow all cells or batteries 234 in the sensor electronics module 126 to be fully charged without overcharging other cells or batteries. In some embodiments, the battery (or batteries) 234 is configured to be charged via an inductive and/or wireless charging pad. One skilled in the art appreciates a variety of known methods of charging batteries, which can be implemented with the system described herein, including wired (cable/plug) and wireless methods.

One or more communication ports 238, also referred to as external connector(s), can be provided to allow communication with other devices, for example a PC communication (com) port can be provided to enable communication with systems that are separate from, or integral with, the sensor electronics module 126. The communication port, for example, may comprise a serial (e.g., universal serial bus or "USB") communication port, allows for communicating with another computer system (e.g., PC, smart mobile phone, personal digital assistant or "PDA," server, or the like). In one exemplary embodiment, the sensor electronics module 126 is able to transmit historical data to a separate computing device for retrospective analysis by a patient and/or physician.

Environmental sensors may also be utilized in accordance with various embodiments. For example, a temperature sensor, e.g., temperature sensor 252, can be used to gauge the temperature of host 120 and/or sensor electronics module 126. A motion sensor 254 can sense or determine movement of the host 120 in which continuous analyte sensor 122 is implanted or to which it is operatively connected. A pressure sensor 256 can be used to detect pressure on continuous analyte sensor 122 and/or pressure on neighboring tissue. It should be noted that more, e.g., other types of sensors or less sensors may be implemented in various embodiments for sensing or detecting changes associated with the host and/or continuous analyte system that might cause one or more fluctuations or changes in a signal.

A clock 258 can regulate the rate at which processor 214 executes instructions. The speed of clock 258 can be configured as needed, as will be described below. Moreover, an offset/calibration module 232 can be circuitry/a logical component(s) used to provide an offset current to shift a received signal at potentiostat 210 when measuring current/counts, as well as calibrate potentiostat 210 for that additional offset current. In one embodiment, the offset current can also be calibrated by offset/calibration module 232.

In conventional continuous analyte sensor systems, the on-skin portion of the sensor electronics is generally simplified to minimize complexity and/or size of on-skin electronics, for example, providing only raw, calibrated, and/or filtered data to a display device 134*a-e* configured to run calibration and other algorithms required for displaying sensor information. In contrast, the sensor electronics module 126 executes prospective algorithms used to generate transformed sensor data and/or displayable sensor information, including, for example, algorithms that: evaluate a clinical acceptability of reference and/or sensor data, evaluate calibration data for best calibration based on inclusion criteria, evaluate a quality of the calibration, compare estimated analyte values with time corresponding measured analyte values, analyze a variation of estimated analyte values, evaluate a stability of the sensor and/or sensor data, detect signal artifacts (noise), replace signal artifacts, determine a rate of change and/or trend of the sensor data, perform dynamic and intelligent analyte value estimation, perform diagnostics on the sensor and/or sensor information, set modes of operation, evaluate the data for aberrancies, and/or the like, which are described in more detail in U.S. Pat. Nos. 7,310,544, 6,931,327, U.S. Patent Publication No. 2005/0043598, U.S. Patent Publication No. 2007/0032706, U.S. Patent Publication No. 2007/0016381, U.S. Patent Publication No. 2008/0033254, U.S. Patent Publication No. 2005/0203360, U.S. Patent Publication No. 2005/0154271, U.S. Patent Publication No. 2005/0192557, U.S. Patent Publication No. 2006/0222566, U.S. Patent Publication No. 2007/0203966 and U.S. Patent Publication No. 2007/0208245, each of which is incorporated herein by reference in its entirety. Furthermore, the sensor electronics module 126 is configured to store the transformed sensor data (e.g., estimated analyte values, trend information) and to communicate the sensor information to a plurality of different display devices 134a-e. In some embodiments, the display devices are configured to display the sensor information as received from sensor electronics module 126, without any additional sensor data processing.

User interface 222 may include a variety of interfaces, such as one or more buttons 224, a liquid crystal display (LCD) 226, a vibrator 228, an audio transducer (e.g., speaker) 230, a backlight (not shown), and/or the like. The components that comprise user interface 222 may provide controls to interact with the user (e.g., the host). One or more buttons 224 may allow, for example, toggle, menu selection, option selection, status selection, yes/no response to on-screen questions, a "turn off" function (e.g., for an alarm), an "acknowledged" function (e.g., for an alarm), a reset, and/or the like. LCD 226 may provide the user with, for example, visual data output. Audio transducer 230 (e.g., a speaker) may provide audible signals in response to triggering of certain alerts, such as present and/or predicted hyperglycemic and hypoglycemic conditions.

Figure 2B:
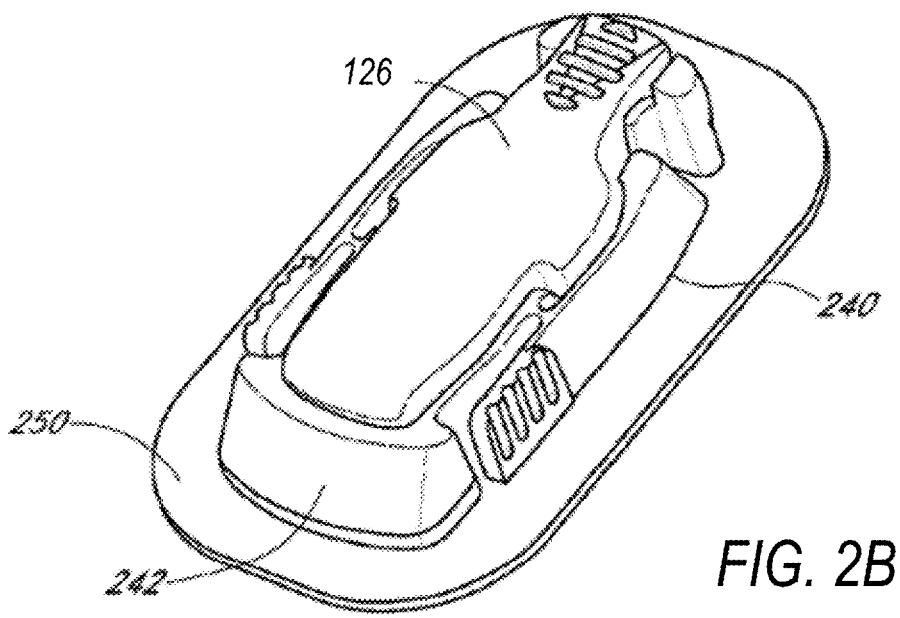
FIGS. 2B and 2C are a perspective view and side view of the example sensor electronics module of FIG. 2A.
Figure 2C:
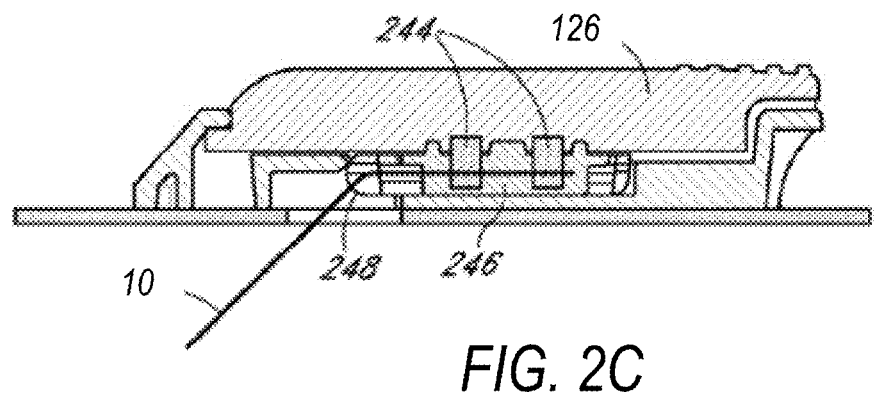

FIGS. 2B and 2C are perspective and side views of analyte sensor system 124 including a mounting unit 240 and sensor electronics module 126 attached thereto in some embodiments, shown in its functional position, including a mounting unit and a sensor electronics module matingly engaged therein. In some embodiments, the mounting unit 240, also referred to as a housing or sensor pod, comprises a base 242 adapted for fastening to a host's skin. The base 242 can be formed from a variety of hard or soft materials, and preferably comprises a low profile for minimizing protrusion of analyte sensor system 124 from host 120 during use. In some embodiments, the base 242 is formed at least partially from a flexible material, which is believed to provide numerous advantages over conventional transcutaneous sensors, which, unfortunately, can suffer from motion-related artifacts associated with movement of host 120, when host 120 is using analyte sensor system 124. The mounting unit 240 and/or sensor electronics module 126 can be located over the sensor insertion site to protect the site and/or provide a minimal footprint (utilization of surface area of the host's skin).

In some embodiments, a detachable connection between the mounting unit 240 and sensor electronics module 126 is provided, which enables improved manufacturability, namely, the relatively inexpensive mounting unit 240 can be disposed of when replacing continuous analyte sensor 122 after its usable life, while the relatively more expensive sensor electronics module 126 can be reusable. In some preferred embodiments, the sensor electronics module 126 is configured with signal processing (programming), for example, configured to filter, calibrate and/or other algorithms useful for calibration and/or display of sensor information, as alluded to previously. However, an integral (non-detachable) sensor electronics module 126 can be configured in accordance with other embodiments.

In some embodiments, the contacts 244 are mounted on or in a subassembly hereinafter referred to as a contact subassembly 246 configured to fit within the base 242 of the mounting unit 240 and a hinge 248 that allows the contact subassembly 246 to pivot between a first position (for insertion) and a second position (for use) relative to the mounting unit 240. The term "hinge" as used herein is a broad term and is used in its ordinary sense, including, without limitation, to refer to any of a variety of pivoting, articulating, and/or hinging mechanisms, such as an adhesive hinge, a sliding joint, and the like; the term hinge does not necessarily imply a fulcrum or fixed point about which the articulation occurs. In some embodiments, the contacts 244 are formed from a conductive elastomeric material, such as a carbon black elastomer, through which continuous analyte sensor 122 extends.

In certain embodiments, the mounting unit 240 is provided with an adhesive pad 250, disposed on the back surface of mounting unit 240 and including a releasable backing layer. Thus, removing the backing layer and pressing the base portion 242 of the mounting unit 240 onto the skin of host 120 adheres the mounting unit 240 to the skin of host 120. Additionally or alternatively, an adhesive pad 240 can be placed over some or all of the analyte sensor system 124 after insertion of continuous analyte sensor 122 is complete to ensure adhesion, and optionally to ensure an airtight seal or watertight seal around the wound exit-site (or insertion site) (not shown). Appropriate adhesive pads can be chosen and designed to stretch, elongate, conform to, and/or aerate the region (e.g., the skin of host 120). The embodiments described with reference to FIGS. 2B and 2C are described in more detail with reference to U.S. Pat. No. 7,310,544, which is incorporated herein by reference in its entirety.

Wireless Communications

Figure 3:
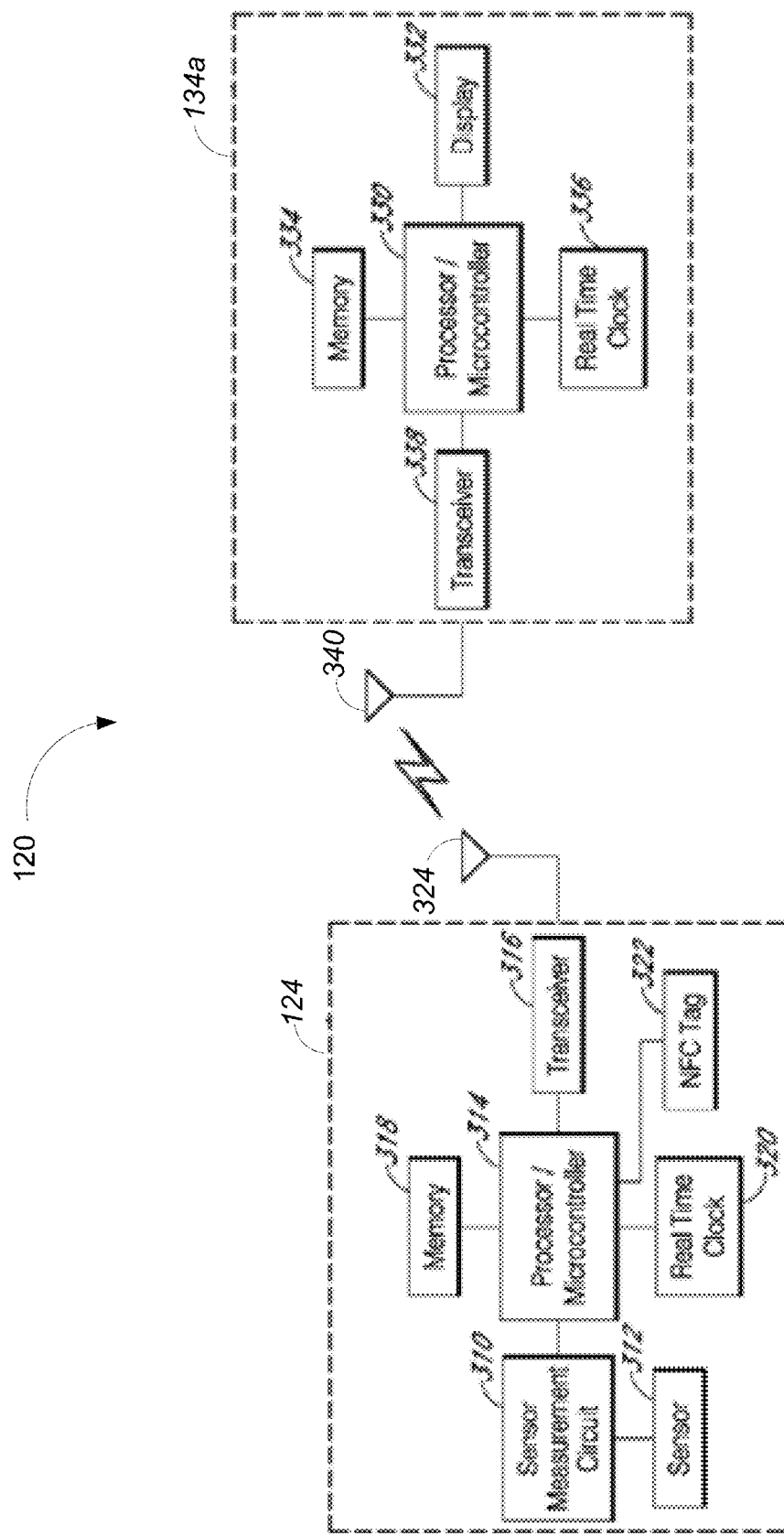
FIG. 3 is a block diagram illustrating elements of an example continuous analyte monitoring system and a display device in communication with each other in accordance with various embodiments of the present disclosure.

FIG. 3 is a block diagram illustrating example components of analyte sensor system 124 and at least one of the plurality of display elements 134a, as well as the communications therebetween. The analyte sensor system 124 may include an implantable continuous analyte sensor 312 (one embodiment of continuous analyte sensor 122 of FIG. 1) coupled to a sensor measurement circuit 310 for processing and managing sensor data. The sensor measurement circuit 310 may be coupled to a processor 314 (part of sensor electronics module 126 in FIG. 1). In some embodiments, the processor 314 may perform part or all of the functions of the sensor measurement circuit 310 for obtaining and processing sensor measurement values from the implantable continuous sensor 312. The processor may be further coupled to a radio unit or transceiver 316 (part of sensor electronics module 126 in FIG. 1 of which telemetry module 232 can be one embodiment) for sending sensor information to and receiving requests and commands from an external device, such as display device 134a, which is used to display or otherwise provide the sensor information to a user. As used herein, the terms "radio unit" and "transceiver" are used interchangeably and generally refer to a device that can wirelessly transmit and receive data. The transmission and receipt of such data further includes utilization of antenna 324. It should be noted that more than one antenna may be utilized in analyte sensor system 124. The analyte sensor system 124 may further include a memory 318 (also part of sensor electronics module 126 in FIG. 1) and a real time clock (RTC) 320 (an example embodiment of clock 205 of FIG. 2A) for storing and tracking sensor information. In some embodiments, analyte sensor system 124 further includes near field communication (NFC) capability. In some embodiments, an NFC tag 322 is implemented/integrated into the electronics in analyte sensor system 124 or embedded in e.g., the housing or mounting unit 240. While not shown explicitly, NFC tag 322 may be included as part of transceiver 316, making transceiver 316 a "smart transceiver."

Wireless communication protocols may be used to transmit and receive data between analyte sensor system 124 and display device 134a. The wireless communication protocol used may be designed for use in a wireless sensor network that is optimized for periodic and small data transmissions (that may be transmitted at low rates if necessary) to and from multiple devices in a close range (e.g., a personal area network (PAN)). For example, the wireless communication protocol may be optimized for periodic data transfers where transceivers may be configured to transmit data for short intervals and then enter low power modes for long intervals. The wireless communication protocol may have low overhead requirements both for normal data transmissions and for initially setting up communication channels (e.g., by reducing header overhead) to reduce power consumption. In some embodiments, burst broadcasting schemes (e.g., one way communication) may be used. This may eliminate overhead required for acknowledgement signals and allow for periodic transmissions that consume little power.

The wireless communication protocol may further be configured to establish communication channels with multiple display devices, e.g., two or more of display devices 134a-e, while implementing interference avoidance schemes. In some embodiments, the wireless communication protocol may make use of adaptive isochronous network topologies that define various time slots and frequency bands for communication with several ones of display devices 134a-e. The wireless communication protocol may thus modify transmission windows and frequencies in response to interference and to support communication with multiple ones of display devices 134a-e. Accordingly, the wireless protocol may use time and frequency division multiplexing (TDMA) based schemes. The wireless communication protocol may also employ direct sequence spread spectrum (DSSS) and frequency-hopping spread spectrum schemes. Various network topologies may be used to support short-distance and/or low-power wireless communication such as peer-to-peer, start, tree, or mesh network topologies such as WiFi, Bluetooth and Bluetooth Low Energy (BLE). The wireless communication protocol may operate in various frequency bands such as an open ISM band such as 2.4 GHz. Furthermore, to reduce power usage, the wireless communication protocol may adaptively configure data rates according to power consumption. Like antenna 324 of analyte sensor system 124, a corresponding antenna 340 is utilized in display device 134a for transmission/receipt of data to/from analyte sensor system 124. Again, one or more antennas in addition to antenna 340 may be used to allow for the various aforementioned communication protocols to operate at their requisite frequencies/frequency ranges.

Display device 134a may be used for alerting and providing sensor information to a user, such as host 120, and may include a processor 330 for processing and managing sensor information. Display device 134a may include a display 332, a memory 334, and a real time clock 336 for displaying, storing and tracking sensor information, respectively. Display device 134a may further include a radio unit or transceiver 338 for receiving sensor information and for sending requests, instructions, and data to the analyte sensor system 124. The transceiver 338 may further employ a wireless communication protocol. The memory 334 may also be used for storing an operating system and/or a custom (e.g., proprietary) application designed for wireless data communication between a transceiver, e.g., transceiver 316 and display device 134a. The memory 334 may be a single memory device or multiple memory devices and may be a volatile or non-volatile memory for storing data and/or instructions for software programs and applications. The instructions may be executed by the processor 330 to control and manage the transceiver 338.

It should be understood that in the case of display device 134e, which may be a medicament delivery device in addition to or instead of a display device, the alerts and/or sensor information provided by continuous analyte sensor 122 vis-à-vis sensor electronics module 126, can be used to initiate and/or regulate the delivery of the medicament to host 120.

In some embodiments, when a standardized communication protocol is used, commercially available transceiver circuits may be utilized that incorporate processing circuitry to handle low level data communication functions such as the management of data encoding, transmission frequencies, handshake protocols, and the like. In these embodiments, processors 314 and 330 do not need to manage these activities, but rather provide desired data values for transmission, and manage high level functions such as power up or down, set a rate at which messages are transmitted, and the like. Instructions and data values for performing these high level functions can be provided to the transceiver circuits 316 and 338, respectively, via a data bus and transfer protocol established by the manufacturer of the transceiver circuits 316 and 338.

Components of analyte sensor system 124 may require replacement periodically. For example, implantable continuous analyte sensor 312 that may be attached to sensor electronics module 126 which itself includes the sensor measurement circuit 310, the processor 314, memory 318, and transceiver 316, and battery (not shown) may require periodic replacement (e.g., every 7-30 days). The sensor electronics module 126 may be configured to be powered and active for much longer than implantable continuous analyte sensor 312 (e.g., for 3 months, 6 months or more) until the battery needs replacement. Replacing these components may be difficult and require the assistance of trained personnel. Reducing the need to replace such components, including the battery if replaceable, significantly improves the convenience of the analyte sensor system 124 to the host 120.

When sensor electronic module 126 is used for the first time (or re-activated once a battery has been replaced in some cases), it may be connected to implantable continuous analyte sensor 312. As will be further described below, there may be a process for initially establishing communication between display device 134a and sensor electronics module 126 when it is first used or re-activated (e.g., the battery is replaced). Once display device 134a and sensor electronics module 126 have established communication, display device 134a and sensor electronics module 126 may periodically and/or continuously be in communication over the life of several ones of implantable continuous analyte sensor 312 until, for example, the battery or the entirety of sensor electronics module 126 needs to be replaced. Each time continuous analyte sensor 312 is replaced, notifications of a new continuous analyte sensor 312 can be sent/exchanged via the previously established communication between the sensor electronics module 126 and display device 134a.

In accordance with one embodiment, analyte sensor system 124 gathers and processes analyte measurements from continuous analyte sensor 312, and periodically sends sensor information representative of the analyte measurements to display device 134a. Measurements are gathered and transmitted over the life of continuous analyte sensor 312 (e.g., in the range of 1 to 30 days or more). New measurements may need to be transmitted often enough to adequately monitor analyte levels. Rather than having the transmission and receiving circuitry of each of the analyte sensor system 124 and display device 134a continuously communicating, the analyte sensor system 124 and display device 134a may regularly and periodically establish a communication channel between them. Thus, analyte sensor system 124 can communicate wirelessly with display device 134a at predetermined time intervals. The duration of the predetermined time interval can be selected to be long enough so that the analyte sensor system 124 does not consume too much power by transmitting data more frequently than needed, yet frequent enough to provide substantially real-time sensor information (e.g., measured analyte values) to one or more of display devices 134a-e for output (e.g., display) to a user. While the predetermined time interval is every five minutes in some embodiments, it is appreciated that this time interval can be varied to be any desired length of time. It should be noted that other contemplated embodiments involve irregular or aperiodic transmissions of sensor information, e.g., from analyte sensor system 124 to one or more of display devices 134a-e.

Fault Detection, Discrimination, Compensation

As alluded to previously, various embodiments detect faults associated with the measurement of analyte concentration in a host and take corrective action so that analyte concentration in the host is represented accurately. Incorrect representation of analyte concentration values, especially as displayed to a user may cause the user to take inappropriate actions, deteriorate the performance of predictive algorithms or closed loop algorithms, and deteriorate the user's trust in the continuous analyte system.

Figure 4A:
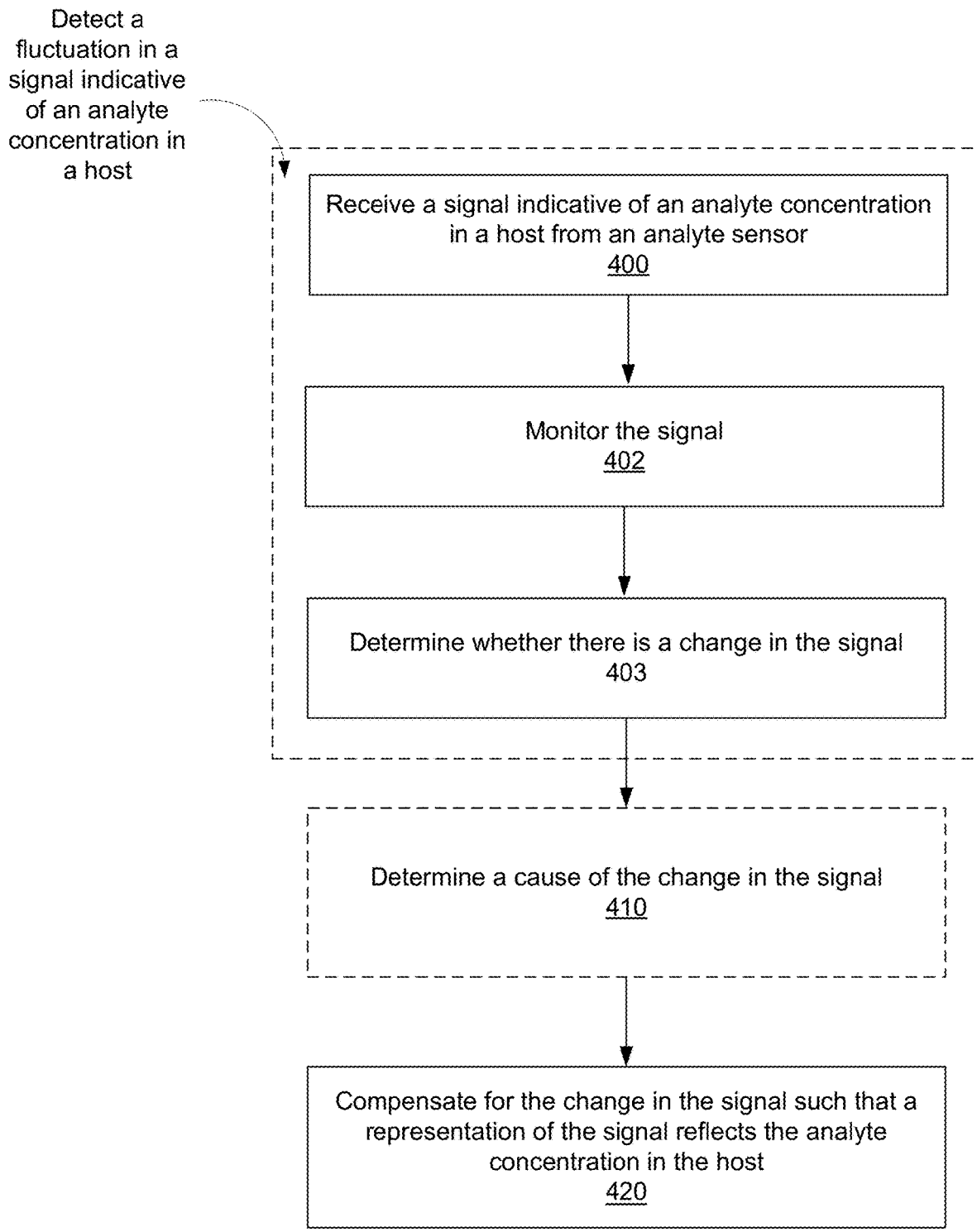
FIG. 4A is a flow chart illustrating example operations performed for compensating for a fluctuation in an analyte concentration signal in accordance with various embodiments of the present disclosure.

FIG. 4A is a flow chart illustrating operations performed in accordance with an example method disclosed herein. At operation 400, a signal indicative of an analyte concentration in a host is received from an analyte sensor. At operation 402, the signal is monitored, and at operation 403, it is determined whether there is a change in the signal. In other words, a fluctuation in a signal indicative of an analyte concentration in a host is detected. At operation 410, a cause of the change or fluctuation in the signal is determined. At operation 420, the change in the signal is compensated for such that the analyte concentration in the host is represented accurately (i.e., a representation of the signal (e.g., a compensated signal) that is indicative of the analyte concentration in the host without noise, for example). In another example, the compensation for the fluctuation may include compensation for one or more types of fluctuation or noise, and the compensated signal may be indicative of the analyte concentration without the one or more types of noise. It should be noted that the order of these steps may vary. For example, one or more of the aforementioned sensors may sense an abnormal condition (e.g., a fluctuation exceeding a predetermined threshold) in continuous analyte monitoring system 100, which can be correlated to a subsequently detected fluctuation in a signal. Specific embodiments addressing fault detection and response are discussed in greater detail below. It should be noted that operation 410 is represented with a hashed line indicating it is an optional operation. That is, and as will be discussed in greater detail below, fluctuations or noise can be compensated for without necessarily needing to determine a cause of the fluctuation or noise beforehand. That is, certain embodiments can detect a fluctuation in a signal and in response, compensate by adjusting the signal in some fashion that renders a more accurate analyte concentration reading.

Fault Detection and Discrimination

Measured analyte, e.g., glucose signals or data received by potentiostat 210 can be affected by various factors. The effect of these various factors are abnormal fluctuations or changes in the measured analyte signals or data, such as large spikes and/or the addition of noise. Thus, various embodiments detect these abnormal fluctuations or changes and account for them. In some embodiments, the cause(s) of the abnormal fluctuations or changes can also be identified and utilized as a basis for compensating for the abnormal fluctuations or changes, and/or gathering information such as statistical information and the like, e.g., for optimizing operation of analyte sensor system 124.

For example, during an electrostatic discharge (ESD) event, or because of regular physical activities/motion performed by the user, measured glucose signals may suffer from severe fluctuations, or even be lost. Additionally, measured analyte signals may be affected due to issues with one or more elements of sensor electronics module 126, e.g., transceiver 316. For example, transceiver 316 may introduce noise into the measured analyte signal thereby affecting the measured analyte signal that is captured by the working electrode during a measurement procedure. As another example, sensor electronics module 126 may experience a power outage due to an unexpected drainage of battery, which may result in the interruption of continuous analyte monitoring.

Regarding the issue of noise, "internal" aspects of analyte sensor system 124, e.g., circuitry such as offset/calibration module 232, can introduce noise into a measured analyte signal by its very nature. That is, noise is a characteristic of all electronic circuits, and the introduction of additional circuitry, such as that comprising offset/calibration module 232 results in noise. For example thermal noise can be introduced due to the thermal motion of electrons, while shot noise can result due to random fluctuations in the current flowing through a circuit(s). Still other noise can result from manufacturing defects or differing quality, e.g., conductance fluctuations. Noise, such as triboelectric noise and parasitic leakage, described below, can also cause issues. Additionally, "external" factors (external referring to factors occurring/originating outside of analyte sensor system 124 (such as host 120), continuous analyte sensor 122, and/or sensor electronics module 126 movement or activity can also cause noise and/or otherwise inaccurate readings. In particular, if sensor electronics module 126 is accidentally pressed or moved due to normal activity of host 120, fluctuation (seen as noise) in the measured analyte signal/observed levels can result.

Figure 4B:
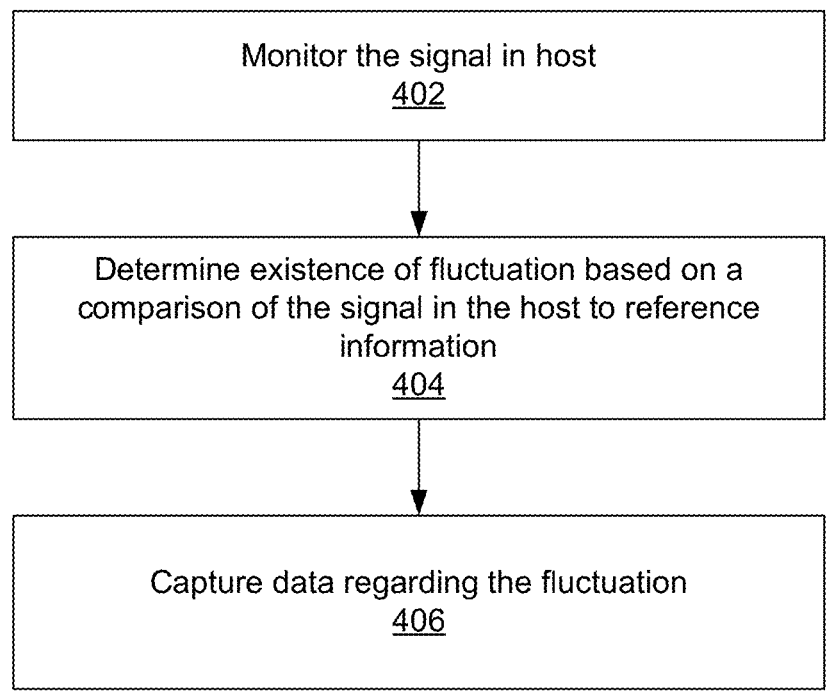
FIG. 4B is a flow chart illustrating example operations performed for detecting a fluctuation in an analyte concentration signal in accordance with various embodiments of the present disclosure.

FIG. 4B illustrates example operations performed in order to detect a fluctuation or change in a signal indicative of an analyte concentration in a host (operations 400, 402, and 403 of FIG. 4A). As previously described, at operation 402, the signal (e.g., a measured glucose signal) in the host is monitored. At operation 404, the existence of the fluctuation is based on a comparison of the signal in the host to reference information (i.e., discrimination). As described above, reference information may be some relevant predetermined threshold, clinical context data, known glucose levels, etc. At operation 406, data regarding the fluctuation is captured. In some embodiments, the capturing of fluctuation data may comprise reducing the sampling rate and/or overclocking ASIC 205 (described in greater detail below) in order to obtain more accurate fluctuation data.

Detection of abnormal fluctuations or changes can be accomplished by discriminating between abnormal or anomalous analyte concentration levels and "normal" or expected analyte concentration levels. Discriminating can include determining if the received signal or the received data matches or meets a predetermined criterion or performing a comparison between clinical context information corresponding to user data that excludes analyte concentration level/measurements. The discriminating may include analyzing the signal using a time-based technique, a frequency-based technique, or a wavelet-based technique. The discriminating may include raw signal analysis, residualized signal analysis, pattern analysis, and/or slow versus fast sampling. The discriminating may include projecting the received signal onto a plurality of templates, each template corresponding to a fault mode. The discriminating may include variability analysis or fuzzy logic analysis. The received clinical context data may be selected from the group consisting of: age, anthropometric data, drugs currently operating on the patient, temperature as compared to a criteria, a fault history of the patient, activity level of the patient, exercise level of the patient, a patient level of interaction with a glucose monitor, patterns of glucose signal values, clinical glucose value and its derivatives, a range of patient glucose levels over a time period, a duration over which patient glucose levels are maintained in a range, a patient glucose state, a glycemic urgency index, time of day, or pressure. The clinical context data may include time since implant, the clinical context criteria may include a range of times since implant in which dip and recover faults are likely. The clinical context data may also include a clinical glucose value and a datum selected from the group consisting of: age, anthropometric data, activity, exercise, clinical use of data, or patient interaction with an analyte monitor. Example systems and methods of discrimination that may be utilized in accordance with various embodiments herein are described in U.S. patent application Ser. No. 14/717,643.

Figure 4C:
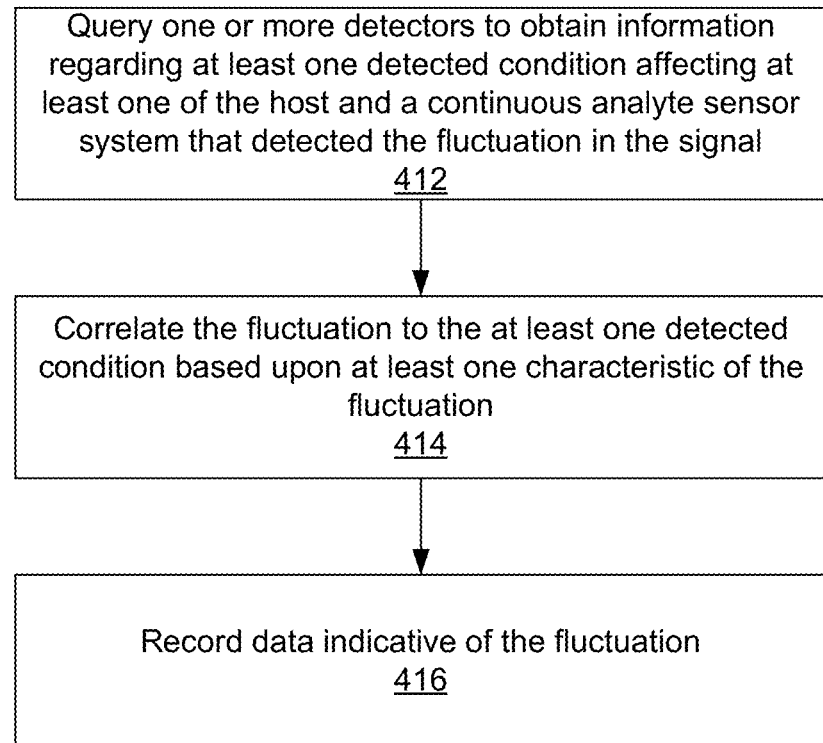
FIG. 4C is a flow chart illustrating example operations performed for determining the cause of a fluctuation in an analyte concentration signal in accordance with various embodiments of the present disclosure.

FIG. 4C illustrates example operations performed when determining the cause of the fluctuation in the signal (operation 410 of FIG. 4A). In general, an attempt is made to correlate the detected fluctuation to a detected condition or occurrence that could give rise to the fluctuation. Accordingly, at operation 412, one or more detectors, e.g., aforementioned temperature sensor 252, motion sensor 254, etc. may be queried to obtain information regarding at least one detected condition affecting at least one of the host and a continuous analyte sensor system that detected the fluctuation in the signal.

For example, pressure sensor 256 can detect pressure or compression using capacitive sensing. Pressure sensor 256 may comprise metal foil embedded in sensor electronics module 126 with opposing metal plates in the bottom of sensor electronics module 126, separated by a compressible membrane. Thus, pressure on sensor electronics module 126 compresses the membrane, thereby changing the capacitance sensed by the opposing metal plates and foil.

Motion sensor 254 may be an accelerometer, such as a 3-axis accelerometer for detecting user activity/motion. Motion sensor 254 could also be used for compression detection, e.g., sensing that sensor electronics module 126 is in an inverted position. Analysis by processor 214 of this sensor data (distinguished from sensor information related to analyte concentration and measured or determined by continuous analyte sensor 122) can result in processor 214 determining that the user is laying on sensor electronics module 126. Processor 214 may then take steps to discriminate (described in greater detail below) as sensor electronics module 126 may give false readings of measured analyte concentration due to lack of oxygen, e.g., the user's tissue area near sensor electronics module 126 gets pushed or pinched. Motion sensor 254 may further comprise a 3-axis compass that can be used in conjunction with the 3-axis accelerometer to better determine the activity level of the user.

Still other external factors, such as sensor drift can result in signal fluctuations. For example, sensor drift can be experienced by continuous analyte sensor 122. Sensor drift can refer to a phenomenon where the sensitivity information (e.g., the relationship between measured current and the glucose level per unit time) may be affected due to changes in temperature. Because temperature can affect the metabolization of glucose, any changes in temperature (whether experienced by the user or analyte sensor system 124) can alter the sensitivity of continuous analyte sensor 122 such that inaccurate glucose measurements or levels may be presented to the user.

Variations in temperature can be due to external factors (e.g., change in the body temperature of the user) and/or internal factors (e.g., change in temperature in the circuitry comprising sensor electronics module 126 or continuous analyte sensor 122 itself). Accordingly, temperature sensor 252 can be used to detect whether sensor drift may be causing faults or fluctuations. In particular, pre-determined knowledge regarding a particular amount of drift associated with a particular temperature or temperature range can be used as a basis for compensating (discussed in greater detail below) for any fluctuation(s) or noise(s) upon detecting the existence or occurrence of that particular temperature or temperature range.

It should be noted that temperature sensor 252 can measure the skin temperature of a host, the tissue neighboring the implantation site of continuous analyte sensor 122, etc. Accordingly, temperature sensor 252 can be implemented in a variety of ways and/or can refer to an array of sensors, including but not limited to the following: an infrared temperature sensor positioned below sensor electronics module 126 (proximate to the host's skin) with a view through mounting unit 240, a thermocouple temperature sensor that protrudes from the bottom of sensor electronics module 126 and through mounting unit 240 to enable contact with the host's skin; a semiconductor temperature sensor embedded in mounting unit 240 to enable direct skin contact. It should further be noted that any sensor itself or data storage memory unit 220 can store sensor manufacturing and calibration information (whether it be temperature sensor 252 or another sensor(s), e.g., motion sensor 254, pressure sensor 256, etc.). Such stored sensor manufacturing and calibration information can include, but is not limited to factory-default calibration settings or information, sensor identification information, etc. Such information can be stored and used for comparison purposes or as, e.g., a baseline or threshold on which sensor electronics module 126 can base a determination(s) of sensor and/or temperature drift, a determination of noise, faults, fluctuations, etc. Further still, temperature sensor 252 can be implemented as a subcutaneous temperature sensor for sensing temperature near or at the tip of continuous analyte sensor 122. The various aforementioned temperature sensors may also be utilized to measure the temperature of other sensors and used for fluctuation-cause correlation and compensation efforts.

Issues, such as spikes in measured glucose values and/or noise can result from liquid ingress. That is, liquid, such as water may seep into sensor electronics module 126 accidentally and cause a fluctuation and/or introduce noise in glucose signals. In particular, water seeping in/at/through sensor electronics module 126 or mounting unit 240, for example, can temporarily cause the measured glucose signal to spike above "normal" levels as introduce noise. For example, water seepage can result in the creation of severe noise followed by a large spike in measured glucose values. After drying out, severe noise may again present itself before a gradual normalizing of the measured glucose values. It should be noted that a moisture sensor (not shown) capable of detecting moisture may be implemented in sensor electronics module 126 and/or as part of mounting unit 240 to sense the presence of liquid. It should be noted that the various sensors described and illustrated herein, e.g., pressure sensor 256, motion sensor 254, etc. may be embodied as separate sensors or as sensors having combined functionalities.

At operation 414, the fluctuation is correlated to the at least one detected condition based upon at least one characteristic of the fluctuation. For example, time, e.g., when the fluctuation occurs, may be used to link the fluctuation with the occurrence of some condition captured by a sensor. Additionally, the type of fluctuation (e.g., internal noise or external noise) and/or amount or frequency of fluctuation (e.g., a big spike due to a sudden nudge or ESD), may provide a basis for correlation. At operation 416, data indicative of the fluctuation is recorded. For example, data regarding when and how the fluctuation was brought about may be captured and recorded to be used to provide a further understanding of the fluctuation in the glucose value (or for later use to compensate or better adjust for a future fluctuation). Recording can occur locally and/or may involve wirelessly transferring the data to a remote server for use/ analysis by technicians, doctors, caretakers, etc. Once fluctuations or changes are detected, a fault can be categorized based on the received signal, the clinical context information, or both where the categorizing the fault includes categorizing the fault as a sensor environment fault or as a system error/artifact fault and/or subcategorizing the fault as, e.g., a compression fault or an early wound response fault. In other words, the cause(s) of the fluctuations or changes can be determined. For example, a fluctuation may arise by determining the existence of some signal criteria, determined by processor 214, to follow some pattern that is not normally associated with physiological changes, e.g., a rate of change of the raw sensor signal (sudden drop). Processor 214 may have knowledge regarding time of day, sensor information indicating that the user may be sleeping (such as from motion sensor 254 sensing an overall lack of motion over some period of time), and that the user may have rolled onto continuous analyte sensor 122 (such as from pressure sensor 256). Upon receiving such sensor data and comparing the sensor data to that information known to processor 214, i.e., time of day, processor 214 can determine that the user is asleep and has rolled onto continuous analyte sensor 122, and it is this that has caused a sudden drop in glucose readings (i.e., due to oxygen deficiency at the site of implantation of continuous analyte sensor 122).

Upon determining the cause(s) of a fault, processor 214 can undertake one or more actions to notify the user or the cause(s) and, e.g., suggest a corrective response. For example, in the event that a sudden drop in glucose readings occurs, and is determined by be the result of the user rolling onto continuous analyte sensor 122 (as discussed above), processor 214 can instruct user interface 222 and/or one or more of display devices 134a-e to trigger an alert or notification. For example, user interface 222 can actuate vibrator motor 228 to alert the user and/or simultaneously display a notification on LCD 226 instructing the user to change position. In this way, the user can take corrective action. Processor 214 may further instruct user interface and/or one or more of display devices 134a-e to notify that user that he/she should wait for more accurate results before taking any corrective action. Further still, information may be gathered about the occurrence of faults and/or the cause of such faults so that processor 214 can better predict or estimate better or more optimal times to transmit EGV data to the one or more display devices 134a-e. For example, processor 214 can invoke a delay prior to sending current EGV data in the event that processor 214 determines that the user has rolled onto continuous analyte sensor 122.

When a fault, e.g., an abnormal or anomalous fluctuation or change in a signal, is detected and the cause(s) of the fault is/are determined, the fluctuation or change in the signal is accounted for such that the analyte concentration in the host is represented accurately.

Compensation

Noise Compensation

As described previously, noise whether from circuitry within analyte sensor system 124 or due to external causes can affect the analyte concentration signal that is captured by the working electrode. Accordingly, various embodiments may utilize an offset to compensate for such noise.

Figure 5A:
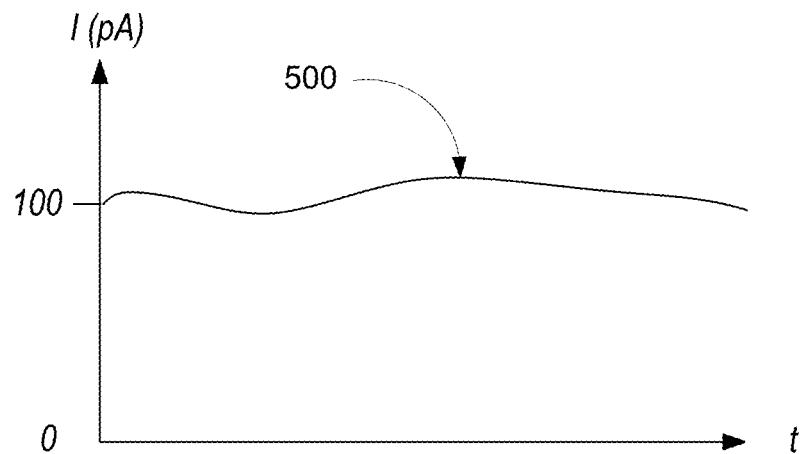
FIGS. 5A, 5B, 5C, and 5D illustrate example an analyte concentration signal and the addition of noise and offset current in accordance with various embodiments of the present disclosure.
Figure 5B:
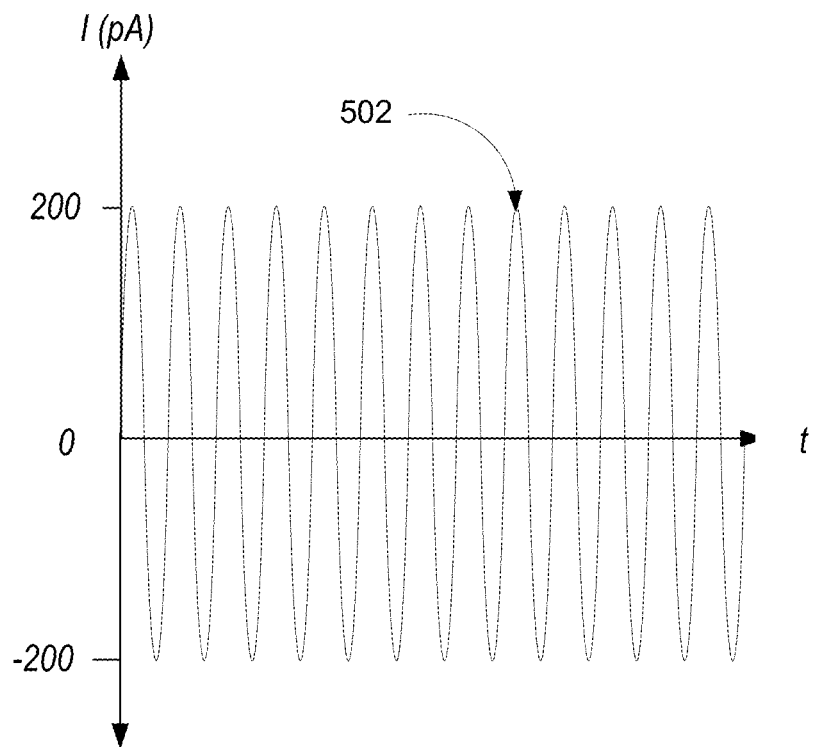

Continuous analyte sensor 122 is generally configured to operate at very low currents (e.g., in the pico-Ampere(pA) range). FIG. 5A is an example graph illustrating a glucose signal 500 (current I in pA) over time t. FIG. 5A shows example analyte measurements at about 100 pA. Noise levels introduced by internal noise sources, such as circuitry and/or the aforementioned triboelectric effect can far exceed that of the glucose signal level, and may also drive the glucose signal level below zero. An example of this is illustrated in FIG. 5B, where, the noise signal 502 oscillates between 200 and −200 pA. In a case where the sensor electronics module 126 is configured to only measure positive signal values, any noise that drives the glucose signal levels below zero is not seen, and would not be compensated for.

Figure 5C:
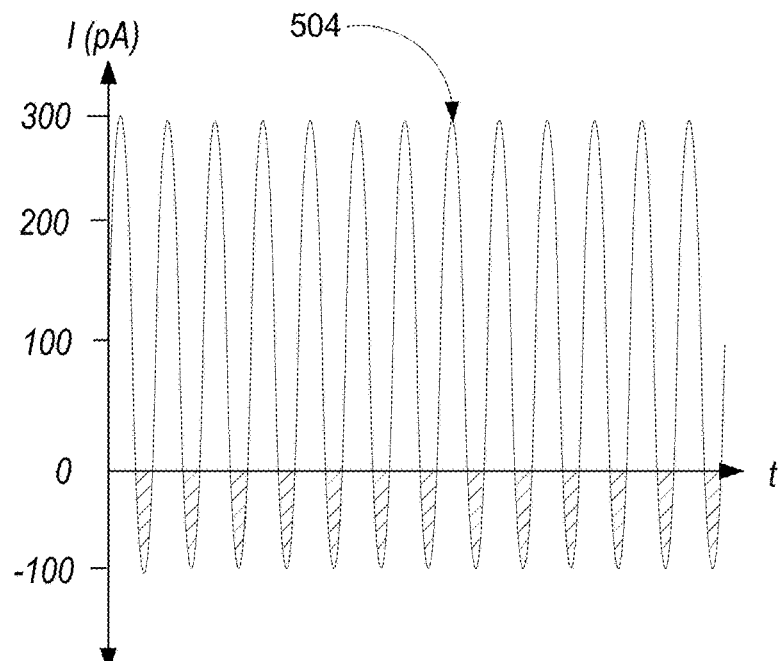

In the example illustrated in FIG. 5C, a measured signal comprising an actual glucose signal, i.e., glucose signal 500, and noise signal 502 is illustrated (i.e., measured signal=glucose signal+noise). Recalling the example glucose signal illustrated in FIG. 5A (glucose signal=100 pA), and the example noise signal illustrated in FIG. 5B (noise oscillating between 200 pA and −200 pA), the resulting signal 504 in FIG. 5C, without any offset oscillates between 300 pA and −100 pA. The portion of the measured signal between 0 pA and −100 pA would not be seen or accounted for. As such, a value obtained from averaging (e.g., filtering) a measured signal (e.g., signal 504) may include error. For example, the averaged value resulting from averaging the measured signal 504 (e.g., in which the negative portion is not accounted for) may erroneously be of a higher value (i.e., positively biased).

Figure 5D:
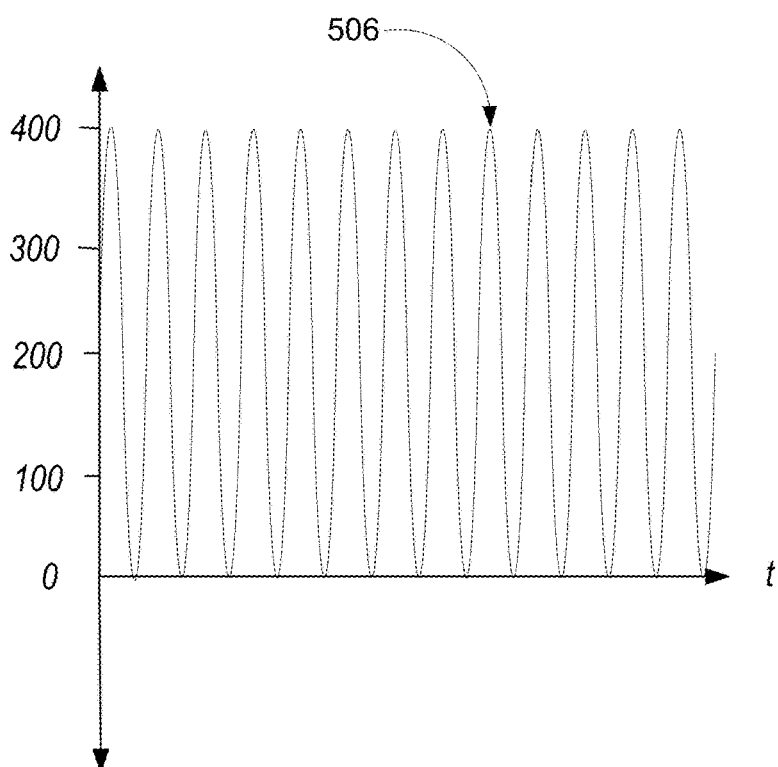

Hence, in some embodiments, an offset current is introduced such that the measured signal, in addition to the actual glucose signal and any noise, also includes an offset (i.e., measured signal=glucose signal+noise+offset). FIG. 5D illustrates an example of such a measured signal 506, where the addition of an offset of, e.g., 100 pA raises the measured signal so that all noise can be captured (none of the measured signal falls below zero) and compensated for. In such an example, averaging the measured signal would yield an accurate value. In some examples, the offset value may be subtracted after averaging the measured signal.

It should be noted that some embodiments utilize a filtering mechanism where the measured signal is averaged. In some cases, as noise increases, the average of the measured signal may be biased in the positive direction. Recalling the above example illustrated in FIG. 5C, any negative portion of the measured signal is not accounted for. This gives rise to an averaging error, as discussed above. Accordingly, various embodiments can also compensate for averaging error through the utilization of an offset circuit.

Triboelectric noise was mentioned previously. The triboelectric effect is a phenomenon where electrical charge is generated by friction between dissimilar materials. In the case of triboelectric noise, the averaged sum would be 0. For example, by capturing all noise present in a measured signal, triboelectric noise would effectively be canceled out. However, in some embodiments, continuous analyte sensor 122 is not capable of capturing negative portion(s) of the measured signal, thus leading to averaging error. Because the measured signal (current) is proportional to glucose concentration, a falsely high reading is problematic (especially if the user were in a hypoglycemic state).

Implementing an offset current can be accomplished through the use of a programmable offset current (e.g., 0 nA, 10 nA, 20 nA, 40 nA). It should be noted that offset currents can range from the order of pico to nano amperes, and the aforementioned offset currents are merely examples. Such a programmable offset current can be implemented during a manufacturing stage by offset/calibration module 232. Alternatively, based on noise measurements, e.g., each time a new continuous analyte sensor 122 is used or during real-time use of analyte sensor system 126, an appropriate offset current can be selected/utilized by offset/calibration module 232. It should be noted that in a scenario where the measured signal comprising a true glucose signal and noise signal oscillate between positive-only values, an offset current need not be utilized. Thus, the aforementioned option to have a 0 nA offset current. In one embodiment, processor 214 may monitor glucose and noise signal values and predetermined threshold values related to such signals, and cause the selection/utilization of an offset current as described herein. In some examples, if a zero-peak value or a percentage of the zero-peak value (e.g., half of the zero-peak value) of a noise signal exceeds that of the glucose signal or the glucose value, processor 214 can monitor the measured signal that includes the glucose and noise signals. Processor 214 can monitor the measured signal continuously, periodically according to some predetermined schedule, aperiodically, or by sampling signals received by potentiostat 210 from continuous analyte sensor 122. Upon processor 214 analyzing the measured signal and determining that the zero-peak value or a percentage of the zero-peak value of the noise signal exceeds the glucose signal or the glucose value, processor 214 instructs offset/calibration module 232 to inject the appropriate offset current.

Again, an offset current shifts up the glucose and noise signals (measured signal) above zero, and any portion of the measured signal that would have been clipped without an offset can be captured. Processor 214 or offset/calibration module 232 can then rely on an appropriate software/algorithm to subtract the known offset from a measured signal, and in some cases, an averaged measured signal, in order to retrieve the true glucose signal level. In some embodiments, processor 214 and/or offset/calibration module 232 may act solely to add offset current, while in other embodiments, processor 214 and/or offset/calibration module 232 can be configured to add offset current and subtract any added offset current.

As previously noted, electrical circuits by their very nature introduce noise. The same then holds true for offset/calibration module 232. That is, the use of offset circuitry in offset/calibration module 232 adds another variable (offset current) to the measured signal which in and of itself can result in the addition of further error/noise if not compensated for. In other words, a true offset value may not be obtained from the offset circuitry. Therefore, some embodiments also compensate for the offset circuitry-introduced noise.

In particular, processor 214 relies on appropriate software/algorithm to "disconnect" or otherwise inhibit operation of the working electrode. Potentiostat 210 (and/or processor 214) may then calibrate for "true zero" (e.g., the offset current. In some cases, the processor 214 and/or the calibration module 232 may cause a calibration procedure for the determination of the offset current. That is, the software/algorithm can disable the external connection (data line 212) to the working electrode so that it can calculate the offset current from the offset/calibration module 232 instead of the normally-calculated current flow between the working electrode and the counter electrode. It should be noted that calibration can be initiated based on some predetermined schedule, after installation of a new continuous analyte sensor 122, etc. Other triggers for initiating calibration can be a trend determined by processor 214 indicating that increasingly more offset current is being introduced over some threshold time. This can be determined by monitoring the number of times offset/calibration module 232 is activated and/or recording the amount of offset current used in data storage memory 220.

Figure 6:
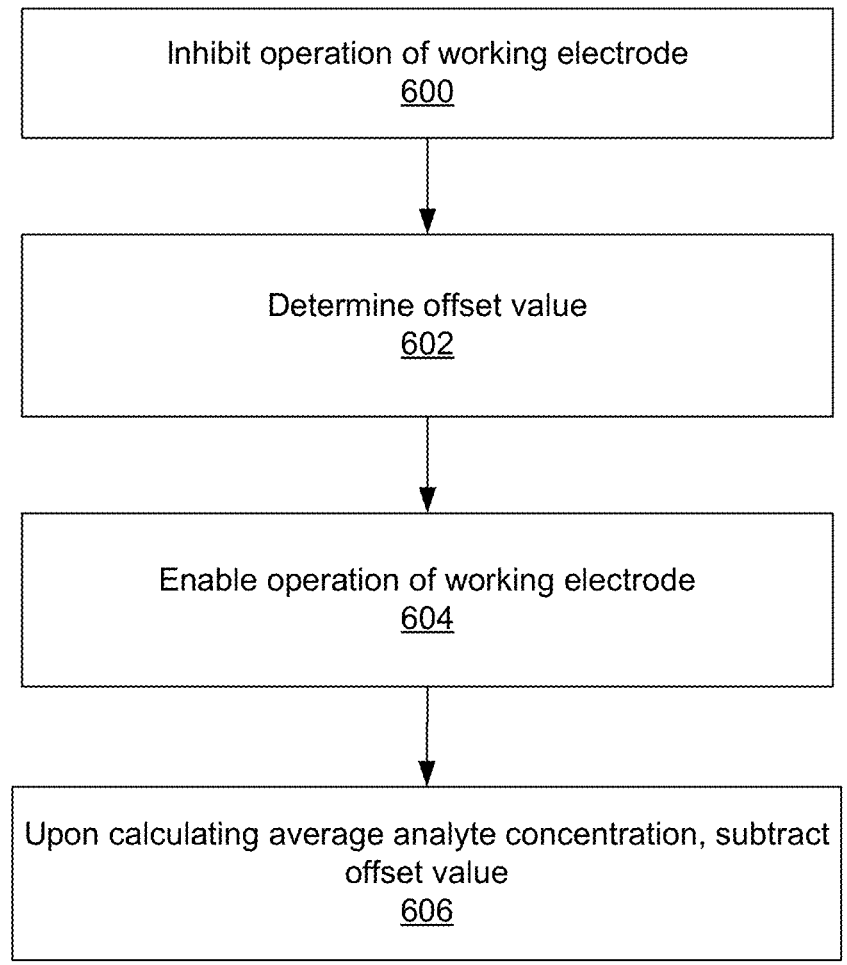
FIG. 6 is a flow chart illustrating example calibration operations performed in accordance with various embodiments of the present disclosure.

FIG. 6 illustrates example operations performed to accomplish offset current compensation calibration in accordance with various embodiments. At operation 600, operation of the working electrode is inhibited. As discussed above, the working electrode is, in effect, disconnected or disabled so that the true zero current can be calculated from offset/calibration module 232 instead of the normally-calculated current flow between the working electrode and the counter electrode. For example, and ignoring noise $$I_{(total,\ i.e.,\ measured)} = I_{(working\ electrode,\ WE)} + I_{(offset)}$$

Upon turning off the working electrode, analyte measurements are no longer being obtained, and the offset value can be determined at operation 602.

$$I_{(measured)} = I_{offset}$$

Once calibrated, the working electrode can be enabled at operation 604. Upon calculating the average analyte concentration levels, the offset value can be subtracted from the averaged result at operation 606, as described previously, in order to retrieve the glucose signal level. That is, processor 214 or offset/calibration module 232 can then rely on an appropriate software/algorithm to subtract the known offset from an averaged measured signal, in order to retrieve the actual glucose signal level.

It should be noted that calibration can be performed in a variety of ways. For example, calibration can be performed on the basis of some predetermined schedule: For example, if it is known that current offset applied varies, but the variation in current offset is for a particular amount over a particular amount of time, calibration may be scheduled accordingly. Alternatively, one-time calibration can be performed (e.g., during manufacturing). Alternatively still, real-time calibration can be performed: For example, if the offset current varies frequently, processor 214 or offset/calibration module 232 can perform additional calibration procedures.

In response, particularly, to noise and/or spikes associated with liquid ingress issues, user-initiated calibration can be performed as a compensatory action. When there is a large jump in estimated glucose value (EGV) data following severe noise (which as discussed above, can result following water ingress, user confidence in the EGV should be considered low. Accordingly, analyte sensor system 124 may prompt the user to perform a calibration of continuous analyte sensor 122 and/or send alerts or question the user regarding, e.g., current activities or otherwise confirm there was an occurrence of accidental water seepage. Moreover, processor 214 may instruct user interface 222 to display a request to the user to enter an independently obtained blood glucose value. If the blood glucose value is vastly different from the EGV, the processor 214 can instruct user interface 222 to alert or warn the user of a potential fault, and to wait for some predetermined time at which time calibration can be performed to ensure continuous analyte sensor 122 is in proper working condition. It should be noted that in some embodiments, the aforementioned alerts and/or questions can be transmitted to and/or provided by one or more of display devices 134a-e. Accordingly, one or more of display devices 134a-3 may have its own user interface including one or more input(s) mechanisms, displays, notification mechanisms, etc.

Another issue that can arise with the introduction of offset current is sensor (temperature) drift. As described above, sensor drift can be experienced by continuous analyte sensor 122 due to changes in temperature. Because temperature can affect the metabolization of glucose, any changes in temperature (whether experienced by the user or analyte sensor system 124) can alter the sensitivity of continuous analyte sensor 122 such that inaccurate glucose measurements or levels may be presented to the user. Thus, temperature calibration can be performed to compensate for temperature drift.

In this instance, the introduction of additional (offset) current can cause temperature drift to occur within sensor electronics module 126, and the resulting temperature differential can adversely impact the offset value. Alternatively, the offset current may suffer from temperature drift that may occur due to the variation of temperature within the circuitry of sensor electronics module 126 itself. To compensate, offset/calibration module 232 can be used during manufacturing (e.g., factory calibration) to account for the variation in the offset value caused by the temperature of sensor electronics module. That is, temperature sensor 252 can be used to capture the temperature variation, and upon sensing a predetermined temperature variation threshold (e.g., indicated in a lookup table, pre-programmed into an appropriate algorithm, etc.), processor 214 can instruct offset/calibration module 232 to perform a calibration procedure. In some embodiments, it can be processor 214 that performs calibration procedures, whether those calibration procedures are calibration procedures initiated due to offset current issues, temperature drifts, etc. It should be noted that calibration as disclosed herein can refer to various types or methods of calibration. In some embodiments, calibration can refer to one-point calibration processes, three-point calibration processes, etc. For example, three-point calibration can be performed for offsets that involve different ranges of values, whereas one-point calibration can be performed, e.g., for addressing temperature drift if sensor electronics module 126 has a single operating temperature/range.

In accordance with another type of compensation, processor 214 may continuously sense temperature (of the host, one or more components of continuous analyte sensor system 124, etc.) and compensate for a change in the glucose information that may be caused by the temperature variation by consulting a lookup table or based upon a real-time algorithm linking glucose levels and/or current values to temperature. Alternatively, processor 214 may consult temperature sensor 252 whenever there is a fluctuation in the measured glucose reading, and compensate for that change according to a given variation in temperature. That is, processor 214 can "directly" compensate for measured analyte levels based upon temperature measurements rather than (or in addition to) compensating for noise as a result of sensor drift. For example processor 214, upon receiving information from temperature sensor 252 that a particular temperature has been sensed, processor 214 can adjust received glucose values in a manner commensurate with the sensed temperature until temperature sensor 252 senses that the temperature has returned to a default value or range. In one embodiment, processor 214 accesses, e.g., a lookup table, to determine an amount by which the received glucose values are to be adjusted based upon a temperature or temperature range.

In accordance with some embodiments, the temperature of sensor electronics module 126 is correlated to the temperature of continuous analyte sensor 122, and the temperature of sensor electronics module 126 is used to correct/compensate for offset current temperature drift faults in analyte concentration readings. For example, processor 214 may receive temperature information from temperature sensor 252 regarding a current temperature of sensor electronics module 126. Processor 214 or offset/calibration module 232 may then update continuous analyte sensor 122 calibration values adjust the continuous analyte sensor 122 calibration values (which might be set for various temperature values). In other words, any change or fluctuation in glucose readings can be sensed and correlated with temperature changes affecting sensor electronics module 126.

Yet another manner of compensation can rely on impedance measurements. Impedance can be utilized as one way to change the characteristics of a sensor. In other words, a change in impedance can be correlated to some change in the sensor. Therefore, based upon impedance, compensatory action can be taken. Impedance can be determined based upon an additional electrode or the working and reference electrodes themselves. For example, when continuous analyte sensor is first inserted into host 120, tissue damage results, so the physiological response to the tissue damage may affect sensor operation. Accordingly, processor 214 may determine the impedance of the reference electrode. Processor 214 may further measure the wound response, e.g., measure the temperature of host 120 so that the wound response and measured impedance can be correlated. In this way, processor 214 may continue measuring impedance, e.g., of the reference electrode, until the impedance returns to a normal or default impedance, at which time, processor 214 may continue with obtaining analyte measurements from continuous analyte sensor 122.

As an alternative to or in combination with some embodiments that utilize an offset current to shift the measured signal (including noise), the sensitivity of continuous analyte sensor 122 can effectively be increased by allowing for high current output. That is, by increasing the current range (i.e., measuring high output current) any noise that may be introduced into the measured (current) signal becomes a small percentage of the total current range. It should be noted that multiple ranges can be covered within one sensor design or with multiple generations of sensors. For example, a plurality of programmable current ranges, e.g., 50 nA, 80 nA, 170 nA, 240 nA may be utilized instead of just one, normally 16 nA, an example of a default current range, where the current ranges would be the sum of the measured glucose signal and any added offset current values. The increased current range can pre-emptively compensate for noise because the percentage of noise relative to the increased current ranges is small. Implementation of these current ranges can be done with software controlled programming registers. In one example, processor 214 may detect the presence of a new analyte sensor 122 in the analyte sensor system 124. Based on the detection, appropriate current ranges may be implemented. For example, the processor 214 may consult a data store that includes information related to various types of sensors and the current ranges for the corresponding types of sensors. Based on the consultation, the processor 214 may implement the appropriate current range for the selected analyte sensor 122.

As discussed above, operation 406 of FIG. 4B involves capturing data regarding the fluctuation, which in the case of noise, may involve taking more accurate measurements of the noise causing the fluctuation by using a faster clock 258 or causing clock 258 to operate faster. More accurate measurement of noise is not limited to detecting fluctuation, but can be used to better compensate for that noise.

In some embodiments, that potentiostat 210 may not always or may not sufficiently capture the details of the noise. Moreover, the large noise signals are generally higher in frequency. In case of non-triboelectric (non-transitory) noise, e.g., when the host lays on continuous analyte sensor 122 and not enough oxygen is being received to allow the enzyme in continuous analyte sensor 122 to metabolize glucose, the measured glucose signal will be abnormal.

To address these issues, a faster sampling rate may be used to capture the details of the noise, such as, details of the triboelectric noise, details of the non-triboelectric/non-transitory noise that doesn't tend to cancel itself out (notwithstanding the use of current offset discussed above), higher sampling (by reducing sampling period and/or overclocking) allows trends/characteristics of noise to be determined which would normally go unnoticed with a slower sampling rate. These identified noise trends/characteristics can be used to better determine cause/source of noise, and appropriate corrective/compensatory action(s) can be performed.

As discussed above, at operation 404, the determination that a fluctuation exists is determined by processor 214 comparing reference information such as previous analyte measurement trends to current analyte measurement values. In the event processor 214 determines the existence of anomalous data or a fluctuation in data, processor 214 can adjust the measurement/sampling period. That is, the measurement/sampling period used by potentiostat 210 can be decreased, e.g., from 30 secs to 2 secs. Additionally, ASIC 205 can be overclocked, e.g., making clock 258 operate faster. For example, at a signal frequency of 0.5 Hz, only one sample is being received every 2 secs. To increase the number of samples that are received, overclocking can be used, where the base frequency of clock 258 (32 kHz) is increased, e.g., by a factor of 2, 4, 8, etc.

Another internal source of noise can come from some artifacts or particles (i.e., some sort of resistance) that are left behind in between the electrodes during the manufacturing process. Because of these artifacts, some current can flow across a potential difference (voltage) due to this resistance provided by the artifacts. This current can in turn, induce error in the measured glucose signal. Therefore, in some embodiments, noise due to parasitic leakage is reduced.

Figure 7:
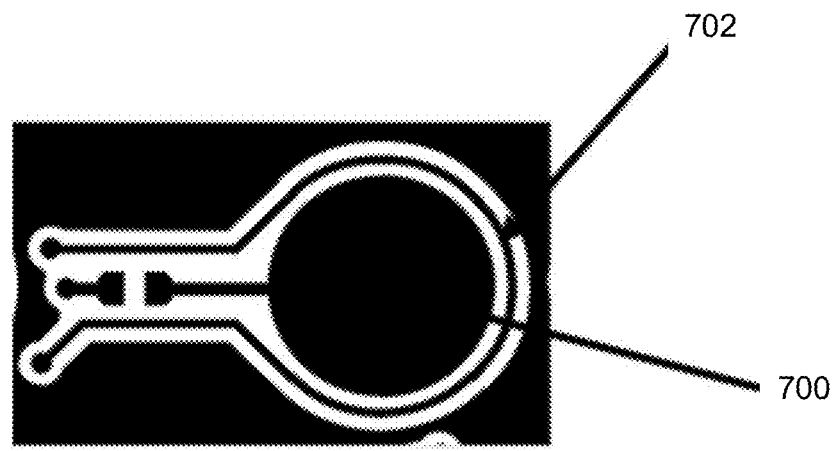
FIG. 7 illustrates the implementation of a guard band in accordance with various embodiments of the present disclosure.

As described above, continuous analyte sensor 122 can have various electrodes which include, e.g., a reference and working/current electrode. Similarly, sensors such as temperature sensor 252, motion sensor 254, pressure sensor 256 also have, e.g., electrodes that connect to a PCB on which ASIC 205 may be implemented. In order to reduce parasitic leakage current, the working electrode signal can be surrounded with a signal of the same voltage potential. That is, the sensor circuitry can be surrounded with an identical voltage potential (guard band) to eliminate the leakage current (e.g., current flow from the working electrode to a ground plane). In other words, potential voltage differences that can cause unnecessary measured current flow are eliminated. FIG. 7 illustrates an example implementation of such a guard band. FIG. 7 shows an electrode 700, around which a guard band 702 is implemented. In one example, processor 214 may monitor various voltage signal values, such as voltage signal values on the sensor electronics module 126, voltage signal values on the electrodes, and further compare the various monitored voltage signal values. The comparison may be performed periodically and/or when a fluctuation in the signals are detected. In one example, the processor 214 or an appropriate entity of the ASIC 205 may then appropriately cause a connection, disconnection, and/or change of voltage potential of the guard band 702. In some examples, the guard band may be implemented on multiple layers of the PCB and surround the working electrodes, where the multiple layers may be connected using vias.

Timing and Battery Fault Compensation

In addition to compensating for noise and/or fluctuations in the measured analyte/glucose signal, some embodiments are also directed to detecting and responding to errors and conditions such as timing errors and battery-related disruptions and faults.

Timing errors can occur when sensor electronics module 126 loses its time due to a disruptive event. In response to such an event, steps can be taken to re-synchronize clock 258. For example, sensor electronics module 126 could experience an ESD event. As a result, EGV data may be transmitted at the wrong time and/or associated with the wrong time stamp. That is, the ESD event can result in a resetting of clock 258, and therefore, EGV data sent subsequently to the occurrence of the ESD even are erroneously timestamped based on the "reset" timestamp instead of the "actual" timestamp.

Figure 8:
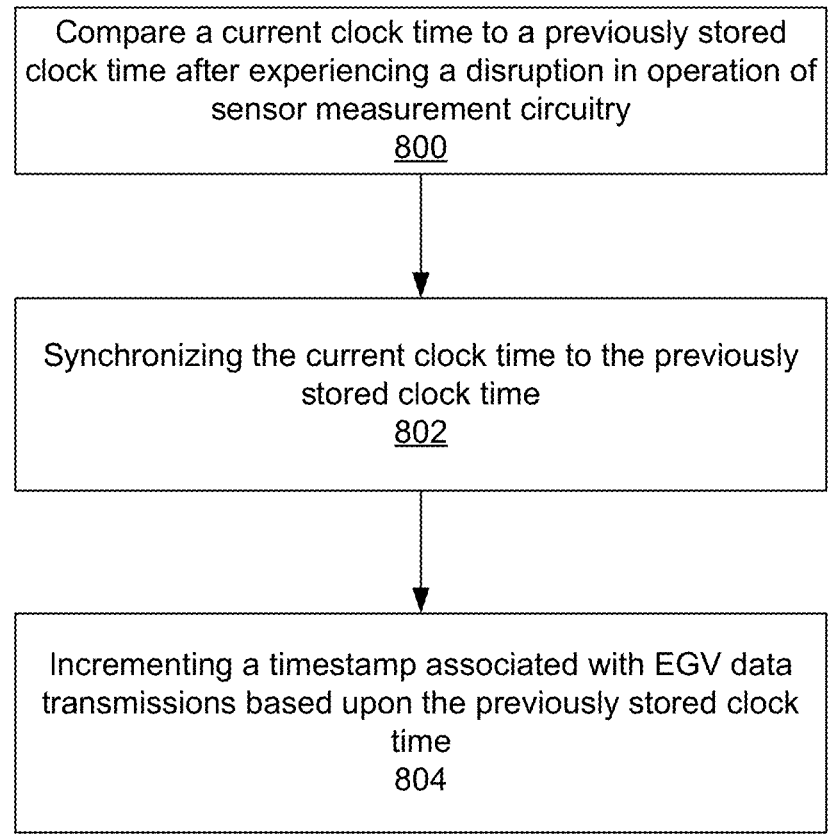
FIG. 8 is a flow chart illustrating example clock resynchronization operations performed in accordance with various embodiments of the present disclosure.

To address this type of timing error, and referring to FIGS. 3 and 8, at operation 800, processor 314 may compare a current clock time (i.e., the time from real time clock 320) to a previously stored clock time after experience a disruption in operation of sensor electronics module 126 (i.e., the stored time in memory 318). Should sensor electronics module 126, for example, lose time due to an ESD event, at operation 802, the current clock time is synchronized to the previously stored clock time, and at operation 804, a timestamp associated with EGV data transmissions are incremented based upon the previously stored clock time. That is, processor 314 can retrieve the stored time from memory 318 and increment based on the stored time rather than that of the real time clock 320. As such, for timestamping purposes, for the next EGV value, this value will be used. Additionally, processor 314 can reset real time clock 320, which can again be used for timestamping the EGV data. It should be noted that data storage memory 220 or some memory of processor 314 may buffer timestamps so that any clock resets can be determined by processor 314, at which point, processor 314 may perform the aforementioned comparison to obtain the "actual" clock/timestamp. Processor 314 may also become aware of ESD events due to other components analyte sensor system 124 resetting or going "offline" for some period of time. Moreover, some type of watchdog circuitry may be implemented to indicate to processor 314 that analyte sensor system 124 is operating correctly. In the event, the watchdog circuit is not "petted" (e.g., by clock 320), processor 314 can assume an event like an ESD event has occurred.

Regarding battery-related errors, ESD events may cause errors in sensor electronics module 126 resulting in abnormally high glucose values due to high current drain. Accordingly, some embodiments detect such high current modes and sensor electronics module 126 can take steps to exit a high current drain mode. In particular, some embodiments monitor the general purpose input/output (GPIO) ports/pins to detect a high current drain mode. In some embodiments, a "proper" battery life profile may be stored in data storage memory 220, for example, so that it can be compared with sample battery life measurements using a comparison algorithm. Sample battery life measurements can be taken and compared with the proper battery life profile based on expected battery life at a particular time (assuming normal or proper usage). In some embodiments, battery 234 may be disconnected from sensor electronics module 406 and connected to an artificial load with known impedance or current-drawing characteristics to determine its current power level. In other embodiments, a Coulomb counter can be used to provide a value indicative of an accumulated amount of charges drawn from battery 234 to determine a current power level. It should be noted that battery 234, like sensor electronics module 126 or its components can fall victim to skewed battery life predictions due to temperature. Accordingly, much like the aforementioned embodiments, where temperature sensor 252 is utilized to determine temperature of sensor electronics module 126, continuous analyte sensor 122, etc., temperature sensor 252 may also be used to determine the operating temperature of battery 234, and the calculated battery life can be compensated or adjusted based on this operating temperature.

This comparison can allow processor 214 to determine that, e.g., a current battery life profile exhibiting a faster decay than expected from the proper battery life profile, which can be indicate that sensor electronics module 126 is experiencing a high current drain mode. Once a high current drain mode is detected, processor 214 may reset sensor electronics module 126. It should be noted that as previously discussed, this may also prompt the resetting or re-synchronization of clock 258 based on a previously stored time. It should be further noted that for ultra-low current devices like sensor electronics module 126, conventional battery monitoring hardware reduces battery life, and the aforementioned comparison algorithm relies on logic for detection which does not impact battery life as much. Such embodiments are also an improvement over using a fuse/circuit breaker because adding such circuitry, as discussed above, can add noise that requires additional compensation.

Figure 9A:
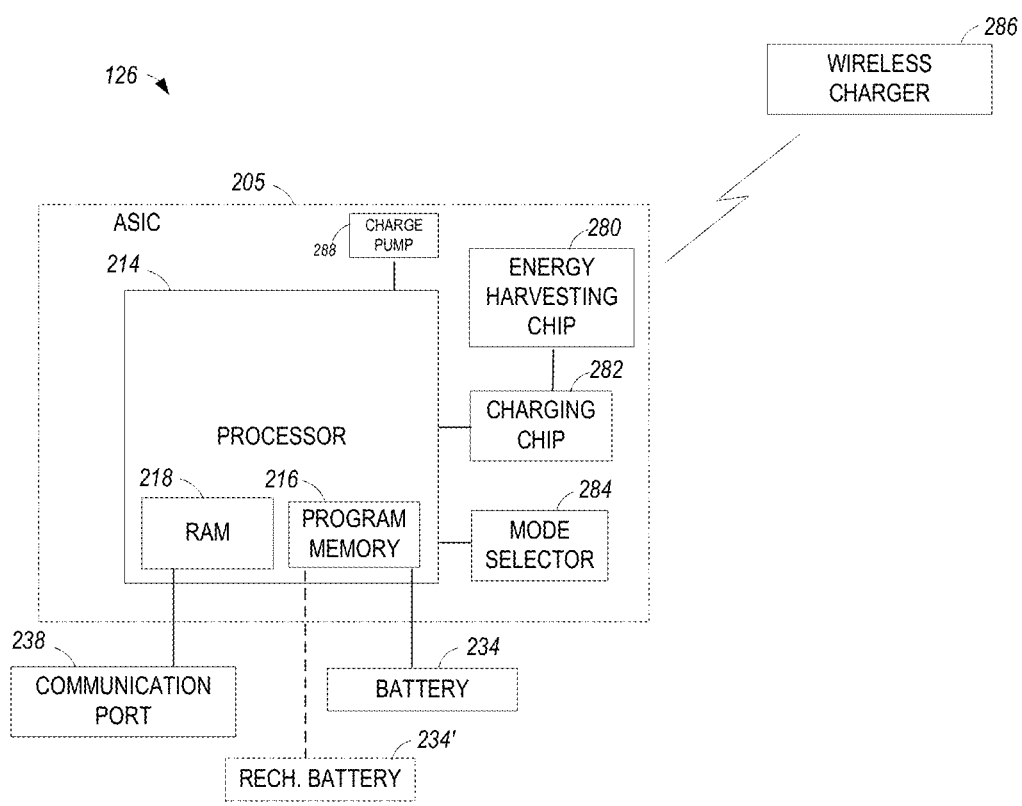
FIG. 9A is a block diagram of battery-related aspects of the example sensor electronics module of FIG. 2A.

During manufacturing, power may be drawn from battery 234, e.g., for testing/quality control purposes. Hence, before sensor electronics module 126 is ever used by the host, it will have already experienced a loss of battery power. Accordingly, some embodiments can switch between a wireless charging mode and a normal, battery-powered mode. In particular, and as illustrated in FIG. 9A, sensor electronics module 126 may have an energy harvesting chip 280 and a charging chip 282 implemented as part of, e.g., ASIC 205. In this way, during a first mode (e.g., during manufacturing), a wireless charger 286 may be used to wirelessly power sensor electronics module 126 thereby avoiding draining battery 234. Energy harvesting chip 280 may harvest power from wireless charger 286 and via charging chip 282, ASIC 205. In a second mode (e.g., during normal use), ASIC 205 can draw power from battery 234. A mode selector 284 can be used to alternate from the first mode to the second mode. Mode selector 284 may be a switch, a logical component, or non-permanent circuitry such as a trace that bypasses battery 234 in the first mode, and allows battery 234 to connect to ASIC 205 in the second mode. In some embodiments, battery 234 may be a rechargeable battery or another rechargeable battery 234' can be used as an additional power source. During the first mode, mode selector 284 can allow for wireless charging of ASIC 205 and/or rechargeable battery 234' to power ASIC 205. During this mode, the rechargeable battery 234' can also be recharged via the wireless charging. In the second mode, battery 234 and/or rechargeable battery 234 can be used to power ASIC 205.

Also during manufacturing, there can be a lack of information or data logging which results in difficulty tracing back battery malfunctioning issues during normal use (by the host). Accordingly, some embodiments employ enhanced data logging to capture details about sensor electronics module 126 and/or battery 234 during the manufacturing stage so that these details can be examined and/or possibly correlated to problems with sensor electronics module 126 and/or battery 234 that occurred during normal use. In particular, processor 214 can log data (in data storage memory 220 or a special partition therein that persists throughout the life of sensor electronics module 126) relating to contract manufacturing steps as well as the status of sensor electronics module 126 and/or battery 234 (e.g., battery levels, reset counts, mode switching, etc.) both before and after being put into storage mode prior to use by the host. Alternatively, such data can be transmitted via communication port 238 along with information identifying the particular sensor electronics module and/or battery to external storage, e.g., to a cloud-based server so as not to impact storage space on data storage memory 220. Later-examination of sensor electronics module 126 and/or battery 234 can be associated with this previously stored data. To this end, battery 234 may have a battery integrated circuit (IC) that can provide identifying information regarding battery 234. This additional data logging need not have a negative impact on the life of battery 234 due to the aforementioned first mode of wireless charging. In addition to logging contract manufacturing steps, data can be gathered, e.g., from temperature sensor 252, to obtain temperature data indicative of temperatures experienced by sensor electronics module 126 and/or battery 234 during the manufacturing process. Moreover, and depending upon received sensor information, test analyte measurement signals, etc. during manufacturing, processor 214 can implement pre-normal usage offsets, calibrations, and other compensatory actions as previously described.

Further still, batteries may have different battery chemistries, batteries may be produced or obtained from different manufacturers. Moreover, different models and/or versions of sensor electronics modules may be used with these different types of batteries. This variability in battery characteristics as well as the characteristics of sensor electronics modules often result in disparate performance characteristics overall. Therefore, some embodiments allow for reconfiguration of configurable parameters at sensor electronics module 126.

In particular, each type or model or set of batteries may have their own unique battery performance characteristics or battery profile. This can include, but is not limited to operating characteristics such as voltage range, continuous current rating, pulse current rating, voltage thresholds, etc. In order to be able to predict when a given battery is going to run out of charge/how long a battery will last in sensor electronics module 126, such battery parameters are used in calculations performed by the firmware/processor in sensor electronics module 126 over the course of the life of sensor electronics module 126. As discussed below, in some embodiments, one or more battery operating parameters (e.g., for different types of batteries) may be transmitted from a server 138 to the sensor electronics module 126 (e.g., via one of the display devices).

Figure 9B:
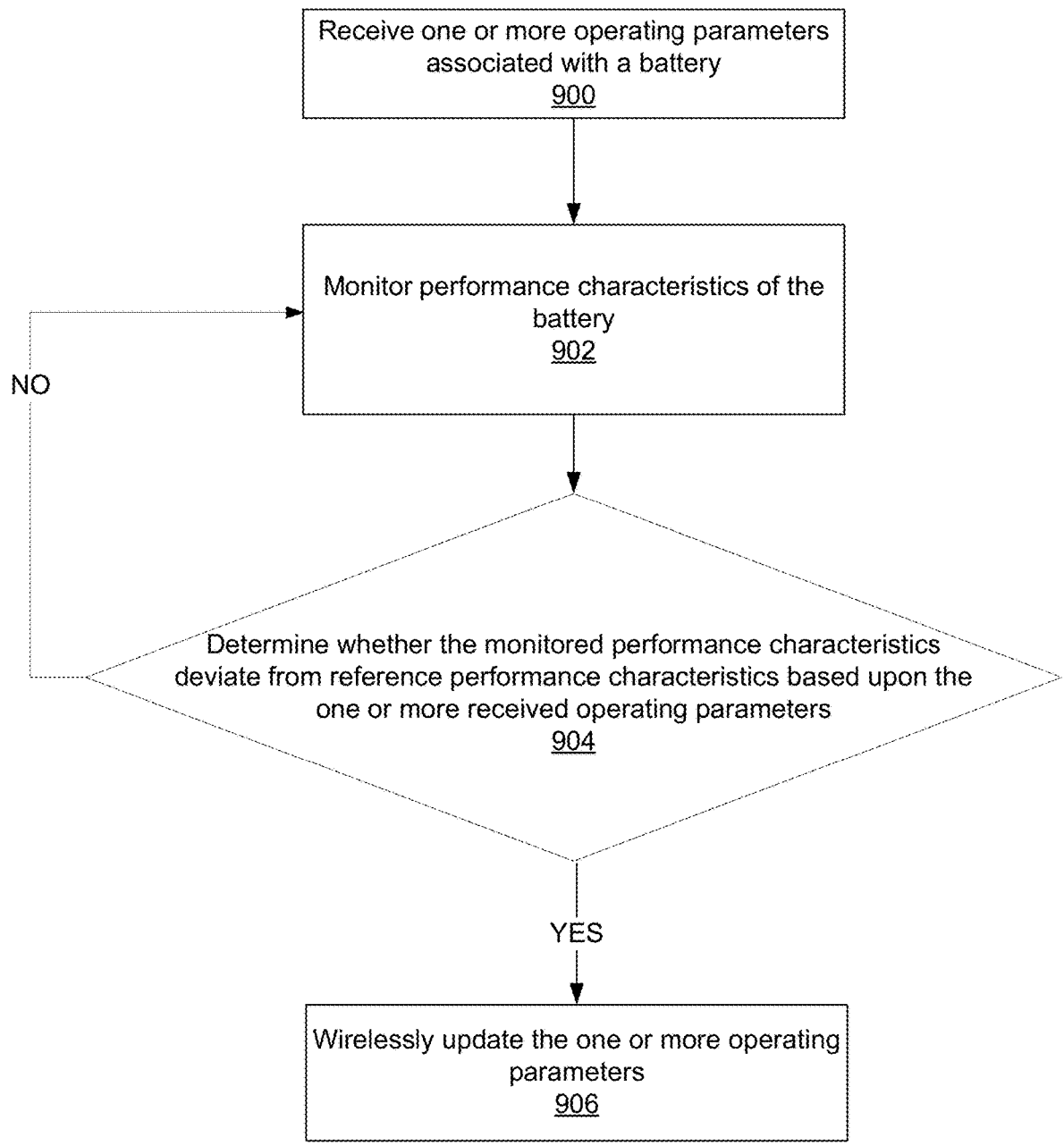
FIG. 9B is a flow chart illustrating example operations performed to accomplish battery configuration in accordance with various embodiments of the present disclosure.

In order to ensure optimum performance of sensor electronics module 126, e.g., avoid unexpected battery drainage and potential disruption in the transmission of sensor information to one or more of display devices 134*a-e*, some embodiments allow sensor electronics module 126 to be updated after battery installation. FIG. 9B illustrates example operations performed by sensor electronics module 126 to accomplish battery configuration. As alluded to previously, one or more operating parameters are received at operation 900. At operation 902, over time, the performance characteristics of the battery, e.g., battery 234, are monitored. At operation 904, sensor electronics module 126 determines whether the monitored performance characteristics of battery 234 deviate from a reference performance (e.g., a known battery profile stored in data storage memory 220) based upon the one or more received operating parameters. If so, at operation 906, the one or more operating parameters can be updated, e.g., wirelessly over communication port 238. In this way, the operation of sensor electronics module 126, e.g., EGV transmission characteristics, connection preferences to one or more of display devices 134*a-e*, and the like can be adapted accordingly in line with the proper performance characteristics of battery 234.

Figure 9C:
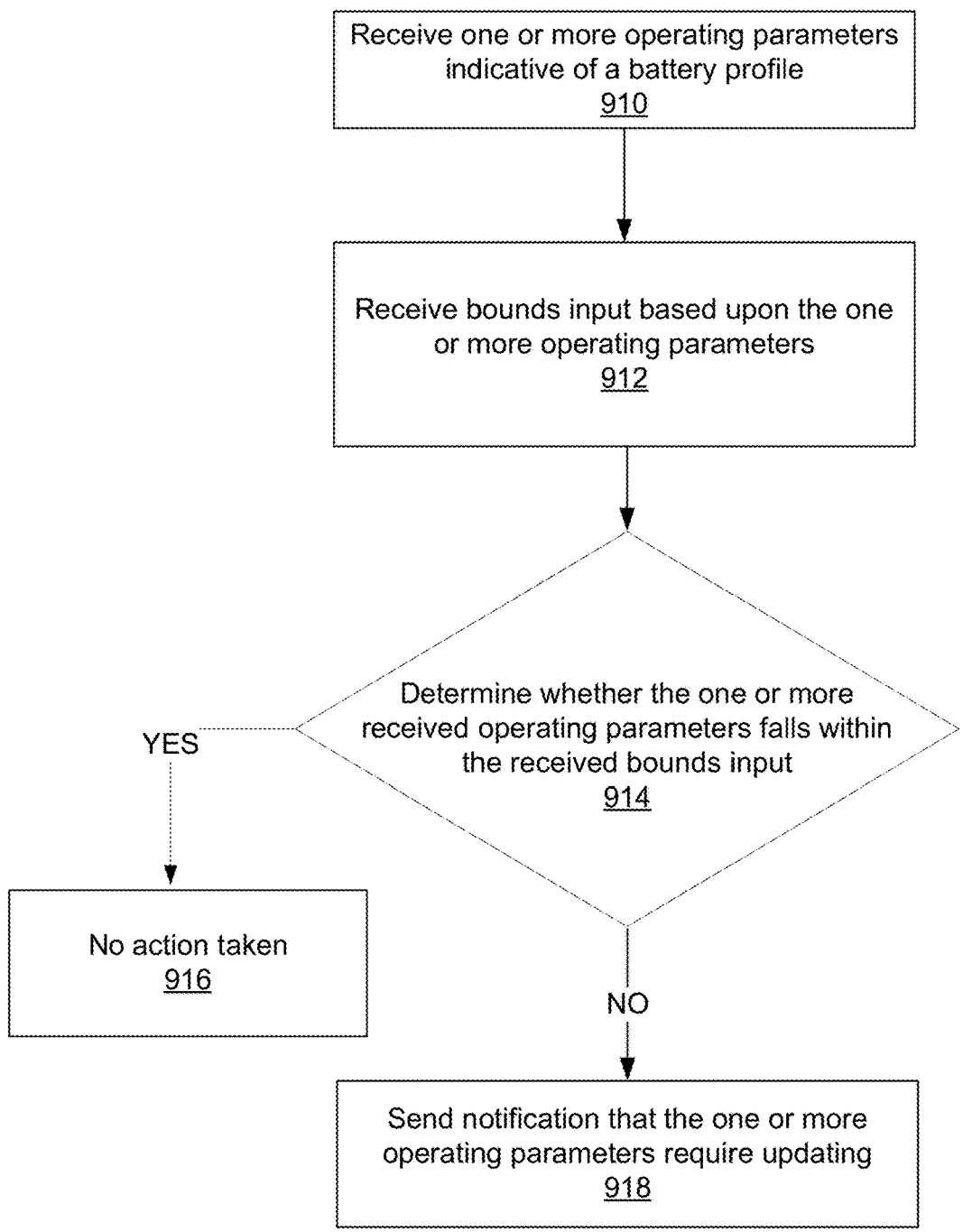
FIG. 9C is a flow chart illustrating example operations performed for utilizing bounds to determine potential battery issues if operating parameters are incorrectly input in accordance with various embodiments of the present disclosure.

In some embodiments, bounds can be used to determine potential battery issues if operating parameters are incorrectly input. That is, and as illustrated in FIG. 9C at operation 910, one or more operating parameters indicative of a battery profile are received by sensor electronics module 126. These operating parameters, examples of which are described above, can be used by the firmware of sensor electronics module 126 to characterize the battery profile. Additionally, bounds are input based upon the one or more operating parameters at operation 912. These bounds can refer to minimum/maximum expected performance characteristics relative to the one or more operating parameters associated with a particular battery. At operation 914, sensor electronics module 126 determines whether the one more operating parameters exceed the bounds input. If not, no action need be taken at 916. That is, if the determination is performed during manufacturing, sensor electronics module 126 can go into a sleep or low power storage mode until powered on by the user. If the determination is performed when sensor electronics module 126 is already operational, it can continue operating. If, however, sensor electronics module 126 determines that the one or more operating parameters that were received exceed the bounds input, processor 214 can instruct user interface 222 or display devices 134*a-e* to display a notification, trip an alarm or otherwise alert the user or manufacturing personnel that the operating parameters require updating at operation 918. In some embodiments, the sensor electronics module may determine when to provide alert notification (e.g., for low battery) based on one of the reconfigurable battery operating parameters (e.g., voltage threshold) for the different types of batteries.

Figure 9D:
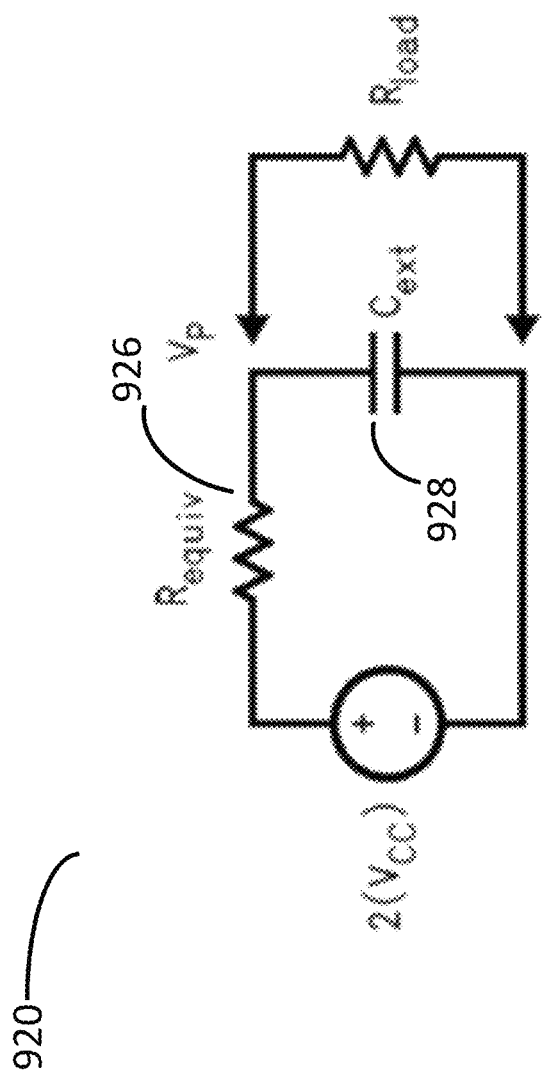
FIG. 9D is a circuit diagram illustrating elements of an example charge pump.

In some embodiments, as shown in FIG. 9A, charge pump 288 may be implemented in the analyte sensor system 124 that may increase (e.g., double) the battery voltage of a single battery (e.g., battery 234) to carry out power intensive operations. As such, in those embodiments, additional batteries may not be needed, thus advantageously saving physical space of the analyte sensor system 124 (i.e., by not installing extra batteries). The charge pump 288 may be internally coupled to the ASIC 205. Moreover, FIG. 9D shows an embodiment of an equivalent model of a charge pump (voltage doubler) 920. For example, in the model 920, an equivalent resistor 926 of resistance, Requiv=1/Cext*Fclock, where Cext is the value of a capacitor 928, and Fclock (Hz) is the frequency of the clock. In one example, with a fixed capacitor value of Cext, the value of Fclock determines the equivalent resistance Requiv of the charge pump 288 or 920—which determines the output current capacity of the charge pump (i.e., how much load it could drive). In other words, the Fclock and the Requiv essentially determines output voltage Vp.

Figure 9E:
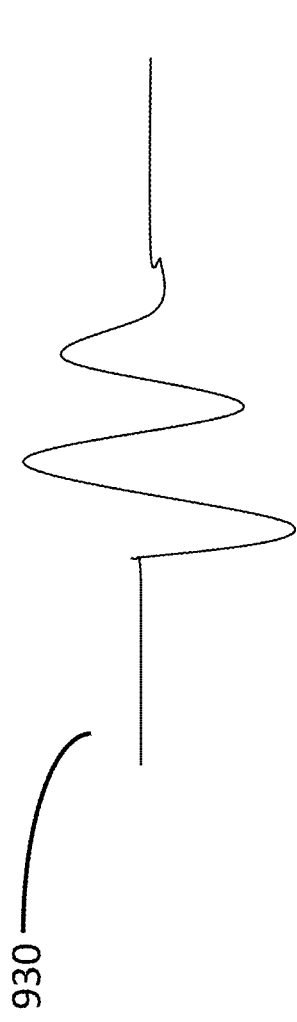
FIG. 9E illustrates an example output voltage with ripples associated with a charge pump in accordance with various embodiments of the present disclosure.
Figure 9F:
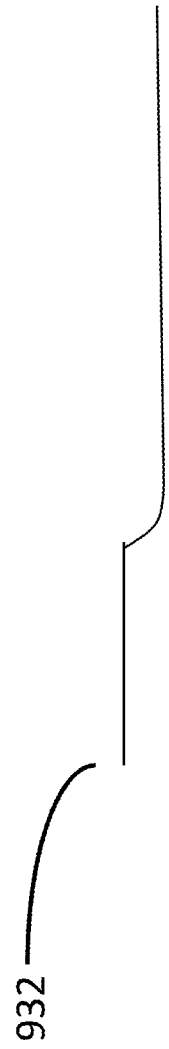
FIG. 9F illustrates an example output voltage without ripples associated with a charge pump in accordance with various embodiments of the present disclosure.

In some implementations, the charge pump may be activated via a feedback control network which may respond to a sudden increase of load by increasing the Fclock frequency. However, due to reactive nature of the control mechanism, the output voltage 930, as shown in FIG. 9E, may have undesired ripples or glitches. In some implementations, the undesired ripples in the output voltage may be eliminated. In such implementations, processor 214 may identify and determine the schedule or timings when the power intensive operations (e.g., wireless transmission of sensor data, and/or accessing internal database of sensor data) occur. In addition, processor 214 may determine the payloads of those operations (e.g., power or current consumptions related to the wireless transmission of sensor data, and/or accessing internal database of sensor data). Based on the schedule and payload information of the operations, the processor 214 may calculate and set the corresponding value of the operating frequency, i.e., Fclock, of the charge pump 920 for the respective operations at their scheduled time according to the payload information. In one example, the processor 214 may access a database for the schedule and the payload information for multiple operations and further store the corresponding calculated operating frequencies Fclock for the respective operations. For example, the processor 214 may instruct the charge pump 288 to operate at one of the calculated frequencies that corresponds to one of the operations (at the predetermined schedule based on the payload information). Implementation of such a process minimizes, or in some cases, eliminates the voltage ripples or glitches in the output voltage 932 (as shown in FIG. 9F) ensuring stable operation of the sensor analyte system 124.

It should also be noted that various combinations of the above-mentioned embodiments/operational scenarios can be combined in different ways to achieve one or more desired operational characteristics in a continuous analyte measurement system. Although various embodiments have been described in the context of continuous analyte measurement, e.g., continuous glucose monitoring, the various embodiments can be adapted for use in other context as well, e.g., for monitoring vital signals.

Figure 10:
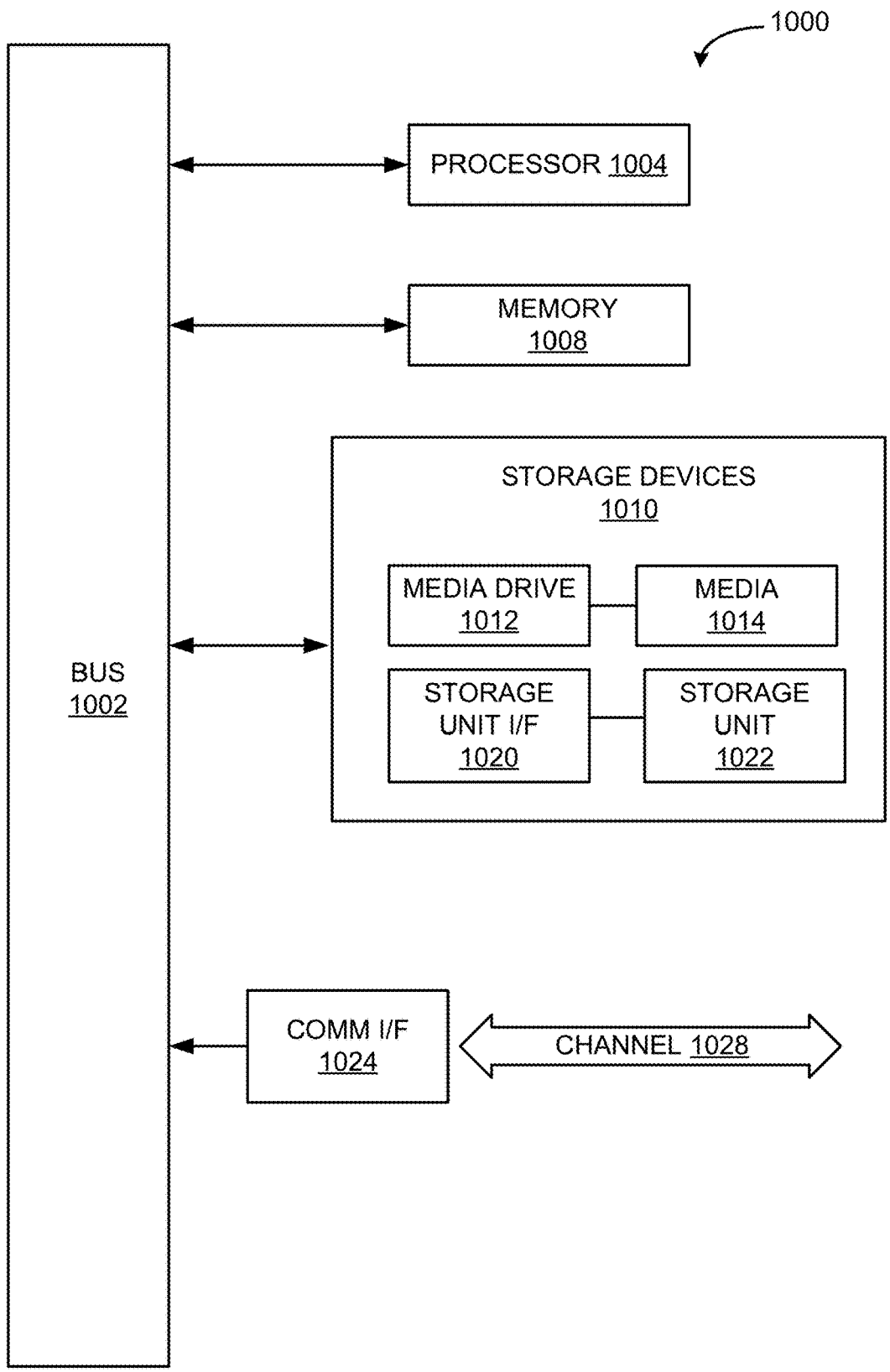
FIG. 10 is a block diagram of an example computing module that may be used to implement various features of embodiments described in the present disclosure.

As used herein, the term module might describe a given unit of functionality that can be performed in accordance with one or more embodiments of the present application. As used herein, a module might be implemented utilizing any form of hardware, software, or a combination thereof. For example, one or more processors, controllers, ASICs, PLAs, PALs, CPLDs, FPGAs, logical components, software routines or other mechanisms might be implemented to make up a module. The modules, circuitry, processors, etc. may be affixed to a printed circuit board (PCB), or the like, and may take a variety of forms. In implementation, the various modules described herein might be implemented as discrete modules or the functions and features described can be shared in part or in total among one or more modules. In other words, as would be apparent to one of ordinary skill in the art after reading this description, the various features and functionality described herein may be implemented in any given application and can be implemented in one or more separate or shared modules in various combinations and permutations. Even though various features or elements of functionality may be individually described or claimed as separate modules, one of ordinary skill in the art will understand that these features and functionality can be shared among one or more common software and hardware elements, and such description shall not require or imply that separate hardware or software components are used to implement such features or functionality.

Where components or modules of the application are implemented in whole or in part using software, in one embodiment, these software elements can be implemented to operate with a computing or processing circuitry capable of carrying out the functionality described with respect thereto. One such example computing module is shown in FIG. 10 which may be used to implement various features of the system and methods disclosed herein. Various embodiments are described in terms of this example computing module 1000. After reading this description, it will become apparent to a person skilled in the relevant art how to implement the application using other computing modules or architectures.

Referring now to FIG. 10, computing module 1000 may represent, for example, computing or processing capabilities found within a self-adjusting display, desktop, laptop, notebook, and tablet computers; hand-held computing devices (tablets, PDA's, smart phones, cell phones, palmtops, etc.); workstations or other devices with displays; servers; or any other type of special-purpose or general-purpose computing devices as may be desirable or appropriate for a given application or environment. For example, computing module 1000 may be one embodiment of one of display devices 134*a-e* or sensor electronics module 126. Computing module 1000 might also represent computing capabilities embedded within or otherwise available to a given device. For example, a computing module might be found in other electronic devices such as, for example, portable computing devices, and other electronic devices that might include some form of processing capability.

Computing module 1000 might include, for example, one or more processors, controllers, control modules, or other processing devices, such as a processor 1004. Processor 1004 might be implemented using a general-purpose or special-purpose processing engine such as, for example, a microprocessor, controller, or other control logic. In the illustrated example, processor 1004 is connected to a bus 1002, although any communication medium can be used to facilitate interaction with other components of computing module 1000 or to communicate externally.

Computing module 1000 might also include one or more memory modules, simply referred to herein as main memory 1008. For example, preferably random access memory (RAM) or other dynamic memory might be used for storing information and instructions to be executed by processor 1004. Main memory 1008 might also be used for storing temporary variables or other intermediate information during execution of instructions to be executed by processor 1004. Computing module 1000 might likewise include a read only memory ("ROM") or other static storage device coupled to bus 1002 for storing static information and instructions for processor 1004.

The computing module 1000 might also include one or more various forms of information storage mechanism 1010, which might include, for example, a media drive 1012 and a storage unit interface 1020. The media drive 1012 might include a drive or other mechanism to support fixed or removable storage media 1014. For example, a hard disk drive, a solid state drive, a magnetic tape drive, an optical disk drive, a compact disc (CD) or digital video disc (DVD) drive (R or RW), or other removable or fixed media drive might be provided. Accordingly, storage media 1014 might include, for example, a hard disk, an integrated circuit assembly, magnetic tape, cartridge, optical disk, a CD or DVD, or other fixed or removable medium that is read by, written to or accessed by media drive 1012. As these examples illustrate, the storage media 1014 can include a computer usable storage medium having stored therein computer software or data.

In alternative embodiments, information storage mechanism 1010 might include other similar instrumentalities for allowing computer programs or other instructions or data to be loaded into computing module 1000. Such instrumentalities might include, for example, a fixed or removable storage unit 1022 and an interface 1020. Examples of such storage units 1022 and interfaces 1020 can include a program cartridge and cartridge interface, a removable memory (for example, a flash memory or other removable memory module) and memory slot, a PCMCIA slot and card, and other fixed or removable storage units 1022 and interfaces 1020 that allow software and data to be transferred from the storage unit 1022 to computing module 1000.

Computing module 1000 might also include a communications interface 1024. Communications interface 1024 might be used to allow software and data to be transferred between computing module 1000 and external devices, such as cloud-based server or other remotely located entity. Examples of communications interface 1024 might include a modem or softmodem, a network interface (such as an Ethernet, network interface card, WiMedia, IEEE 802.XX or other interface), a communications port (such as for example, a USB port, IR port, RS232 port Bluetooth® interface, or other port), or other communications interface. Software and data transferred via communications interface 1024 might typically be carried on signals, which can be electronic, electromagnetic (which includes optical) or other signals capable of being exchanged by a given communications interface 1024. These signals might be provided to communications interface 1024 via a channel 1028. This channel 1028 might carry signals and might be implemented using a wired or wireless communication medium. Some examples of a channel might include a phone line, a cellular link, an RF link, an optical link, a network interface, a local or wide area network, and other wired or wireless communications channels.

In this document, the terms "computer program medium" and "computer usable medium" are used to generally refer to transitory or non-transitory media such as, for example, memory 1008, storage unit 1020, media 1014, and channel 1028. These and other various forms of computer program media or computer usable media may be involved in carrying one or more sequences of one or more instructions to a processing device for execution. Such instructions embodied on the medium, are generally referred to as "computer program code" or a "computer program product" (which may be grouped in the form of computer programs or other groupings). When executed, such instructions might enable the computing module 1000 to perform features or functions of the present application as discussed herein.

Methods and Systems

The following methods, sensor electronics, and systems are provided.

Method 1: A computer-implemented method, comprising: receiving a signal indicative of an analyte concentration in a host from an analyte sensor; monitoring the signal; determining whether there is a change in the signal; and compensating for the change in the signal such that a representation of the signal is at least indicative of the analyte concentration in the host.

Method 2: An embodiment of Method 1, further comprising determining a cause of the change in the signal.

Method 3: An embodiment of Method 2, wherein determining the cause of the change in the signal comprises correlating the change in the signal to an event identified by one or more sensors of an analyte sensor system.

Method 4: An embodiment of Method 2 or 3, further comprising at least one of recording and transmitting to at least one of a remote server, a local data storage memory, and a display device, information regarding at least one of the cause of the change in the signal and the change in the signal.

Method 5: An embodiment of Method 1 wherein the change in the signal comprises a noise signal component added to the signal indicative of the analyte concentration in the host.

Method 6: An embodiment of Method 5, wherein a source of the noise signal component is internal to an analyte sensor system through which the analyte concentration in the host is determined.

Method 7: An embodiment of Method 6, wherein the source of the noise signal component comprises circuitry internal to the analyte sensor system.

Method 8: An embodiment of Method 5, wherein accounting for the change in the signal comprises adding an offset current to the signal indicative of the analyte concentration in the host and the noise signal component such that the signal indicative of the analyte concentration in the host and the noise signal component are shifted by an amount commensurate with the offset current.

Method 9: An embodiment of Method 5, further comprising relatively reducing the noise signal component by increasing sensitivity of an analyte sensor for measuring the analyte concentration in the host.

Method 10: An embodiment of Method 9, wherein increasing the sensitivity of the analyte sensor comprises increasing a current range over which the analyte sensor operates.

Method 11: An embodiment of Method 8, wherein a source of the noise signal component comprises the added offset current.

Method 12: An embodiment of Method 11, further comprising performing a calibration procedure to determine the offset current by at least compensating for the noise signal component resulting from the addition of the offset current.

Method 13: An embodiment of Method 12, wherein the performance of the calibration procedure comprises inhibiting operation of a working electrode of an analyte sensor for measuring the analyte concentration in the host to enable measurement of only the offset current.

Method 14: An embodiment of Method 13, wherein the performance of the calibration procedure further comprises enabling operation of the working electrode and measuring the analyte concentration in the host which includes the offset current and subtracting the measured offset current from the measured analyte concentration in the host.

Method 15: An embodiment of Method 14, wherein the calibration procedure is performed in accordance with one of a predetermined schedule, on a one-time basis, or in real-time.

Method 16: An embodiment of Method 1, wherein the change in the signal comprises a fluctuation caused by temperature drift of an analyte sensor for measuring the analyte concentration in the host.

Method 17: An embodiment of Method 16, further comprising performing temperature calibration to compensate for variations in an offset current added to the signal indicative of the analyte concentration in the host due to temperature.

Method 18: An embodiment of Method 16, wherein the temperature drift of the analyte sensor is determined based upon an impedance measurement of a reference electrode of the analyte sensor.

Method 19: An embodiment of Method 5, further comprising capturing details of the noise signal component by reducing at least one of a sampling period during which the analyte concentration in the host is measured and overclocking circuitry of an analyte sensor for measuring the analyte concentration in the host.

Method 20: An embodiment of Method 5, wherein a source of the noise signal component comprises artifact-induced current flow across a voltage differential between at least two electrodes of an analyte sensor for measuring the analyte concentration in the host.

Method 21: An embodiment of Method 5, further comprising implementing a guard band having the same voltage differential to compensate for artifact-induced current flow.

Method 22: An embodiment of Method 5, wherein a source of the noise signal component is external to an analyte sensor system through which the analyte concentration in the host is determined.

Method 23: An embodiment of Method 22, further comprising sensing the noise signal component external to the analyte sensor system via one or more sensors, and compensating for the noise signal component by at least one of adding an offset current to the signal indicative of the analyte concentration in the host and the noise signal component and performing a calibration procedure to determine the offset current by compensating at least for the noise signal component resulting from the addition of the offset current.

Method 24: An embodiment of Method 1, wherein the change in the signal comprises a spike in the analyte concentration in the host.

Method 25: An embodiment of Method 24, further comprising directly adjusting analyte concentration values by a predetermined adjustment amount based upon one or more factors causing the spike.

Method 26: A method comprising: comparing a current clock time to a previously stored clock time after experiencing a disruption in operation of sensor measurement circuitry in an analyte sensor system; synchronizing the current clock time to the previously stored clock time; and incrementing a timestamp associated with EGV data transmissions based upon the previously stored clock time.

Method 27: An embodiment of Method 26, wherein a real-time clock from which the current clock time is determined is reset due to the disruption in the operation of the sensor measurement circuitry, and wherein the disruption in the operation of the sensor measurement circuitry comprises an electrostatic discharge event.

System 28: A system comprising: an analyte sensor adapted to transmit analyte concentration data; sensor measurement circuitry adapted to receive analyte concentration data from the sensor and detect a change in the analyte concentration data, wherein the sensor measurement circuitry compensates for a fluctuation exceeding a pre-determined threshold in the analyte concentration data.

System 29: An embodiment of System 28, further comprising at least one of memory adapted to store information associated with the fluctuation in the analyte concentration data and a transmitter adapted to transmit the information associated with the fluctuation to at least one of a remote server and a display device adapted to display the information associated with the abnormal fluctuation or information derived therefrom.

System 30: An embodiment of System 28 or 29 comprising one or more environmental sensors to determine environmental conditions potentially causing the fluctuation in the analyte concentration data.

System 31: An embodiment of System 28 or 29, further comprising offset current circuitry adapted to add an offset current to a signal indicative of the analyte concentration data and a noise signal component associated with the fluctuation such that the signal indicative of the analyte concentration data and the noise signal component are shifted to levels above a zero value.

System 32: An embodiment of System 31, where the offset current circuitry is triggered to add the offset current upon a determination that a zero-peak value associated with the noise signal component is greater than the signal indicative of the analyte concentration data.

System 33: An embodiment of System 31, wherein the offset current circuitry adds the offset current in accordance with one or more programmed offset currents.

System 34: An embodiment of System 33, further comprising a processor adapted to compensate for the noise signal component and subtract the added offset current from the received analyte concentration data to obtain analyte concentration data indicative of an actual analyte concentration absent the noise signal component.

System 35: An embodiment of System 34, wherein the processor is further adapted to capture details of the noise signal component by reducing at least one of a sampling period during which the analyte concentration data is measured and overclocking circuitry of the analyte sensor.

System 36: An embodiment of System 28, further comprising a guard band having the same voltage differential as that existing between at least two electrodes of the analyte sensor to compensate for artifact-induced current flow across the voltage differential.

System 37: An embodiment of System 28, further comprising a processor adapted to directly adjust analyte concentration data by a predetermined adjustment amount based upon one or more factors causing the abnormal fluctuation.

Sensor Electronics 38: Sensor electronics, comprising: a processor; and an offset circuit configured to apply an offset current to a received analyte concentration signal affected by noise upon a determination by the processor of the existence of the noise.

Sensor Electronics 39: An embodiment of Sensor Electronics 38 further comprising calibration circuitry, wherein the calibration circuitry determines the offset current by compensating for noise caused by the offset circuit.

Sensor Electronics 40: An embodiment of Sensor Electronics 39, wherein one of the processor or the calibration circuity inhibits operation of a working electrode of an analyte sensor for measuring the analyte concentration in the host resulting in the analyte concentration signal to enable measurement of only the offset current.

Sensor Electronics 41: An embodiment of Sensor Electronics 39, wherein one of the processor or the calibration circuity enables operation of the working electrode and measures the analyte concentration in the host which includes the offset current and subtracting the measured offset current from the measured analyte concentration in the host.

Sensor Electronics 42: An embodiment of Sensor Electronics 39, wherein one of the processor or the calibration circuitry performs temperature calibration to compensate for variations in the offset current due to temperature.

Sensor Electronics 43: An embodiment of Sensor Electronics 39, further comprising an energy harvesting chip, a charging chip, and a mode selector for switching between a wireless charging mode and a battery powered mode.

Sensor Electronics 44: An embodiment of Sensor Electronics 43, wherein a wireless charger wirelessly powers the sensor electronics during a first mode via the energy harvesting chip adapted to harvest power from the charging chip.

Sensor Electronics 45: An embodiment of Sensor Electronics 44, wherein a battery powers the sensor electronics in a second mode, and wherein the battery is bypassed in the first mode.

Method 46: A method, comprising: receiving one or more operating parameters associated with a battery at a processor of a system operating under power provided by the battery; monitoring performance characteristics of the battery; determining whether the monitored performance characteristics deviate from reference performance characteristics based upon the one or more received operating parameters; and wirelessly updating the one or more operating parameters upon a determination that the monitored performance characteristics deviate from the reference performance characteristics.

Method 47: An embodiment of Method 46, wherein the reference performance characteristics comprise a known profile associated with the battery.

Method 48: An embodiment of Method 46, further comprising adapting operation of sensor electronics powered by the battery in accordance with the updated performance characteristics of the battery.

Method 49: A method, comprising: receiving one or more operating parameters indicative of a battery profile at a processor controlling sensor measurement circuitry; receiving bounds input based upon the one or more operating parameters; determining whether the one or more received operating parameters falls within the received bounds input; and sending a notification to a user interface associated with the sensor measurement circuitry that the one or more operating parameters require updating upon a determination that the one or more received operating parameters fall outside of the received bounds input.

Method 50: An embodiment of Method 49, wherein the bounds input comprises minimum and maximum expected performance characteristics associated with the one or more operating parameters.

Method 51: A method comprising: determining a schedule information of an operation of an analyte sensor system; identifying a payload information associated with the operation; calculating an operational frequency of a charge pump according to the payload and schedule information; and instructing the charge pump to operate at the calculated operational frequency during an occurrence of the operation.

Method 52: An embodiment of Method 51, wherein the operation includes transmission of sensor data from the analyte sensor system.

While the disclosure has been illustrated and described in detail in the drawings and foregoing description, such illustration and description are to be considered illustrative or exemplary and not restrictive. The disclosure is not limited to the disclosed embodiments. Variations to the disclosed embodiments can be understood and effected by those skilled in the art in practicing the claimed disclosure, from a study of the drawings, the disclosure and the appended claims.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the present disclosure, but instead as merely intended to highlight alternative or additional features that may or may not be utilized in a particular embodiment. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit, and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the present disclosure to the specific embodiments and examples described herein, but rather to also cover all modification and alternatives coming with the true scope and spirit of the present disclosure.

What is claimed is:

1. A system comprising:
    an analyte sensor adapted to measure analyte concentration data;
    sensor measurement circuitry adapted to receive analyte concentration data from the analyte sensor and detect a fluctuation including noise in the received analyte concentration data, wherein the sensor measurement circuitry is further adapted to compensate for the detected fluctuation exceeding a predetermined threshold in the analyte concentration data to accurately reflect analyte concentration in a host; and
    an offset current circuit adapted to add an analog current to a signal indicative of the analyte concentration data and a noise signal component associated with the noise such that the signal indicative of the analyte concentration data and the noise signal component are shifted from below-zero levels to levels above a zero value, wherein the offset current circuit is configured to be triggered to add the analog current upon a determination that a percentage of zero-peak value associated with the noise signal component is greater than the signal indicative of the analyte concentration data.

2. The system of claim 1, further comprising at least one of memory adapted to store information associated with the fluctuation in the analyte concentration data or a transmitter adapted to transmit the information associated with the fluctuation to at least one of a remote server or a display device adapted to display the information associated with the fluctuation or information derived therefrom.

3. The system of claim 2, comprising one or more environmental sensors to determine environmental conditions configured to cause the fluctuation in the analyte concentration data.

4. The system of claim 1, wherein the offset current circuit is adapted to add the analog current in accordance with one or more programmed offset currents.

5. The system of claim 4, further comprising a processor adapted to compensate for the noise signal component and subtract the added analog current from the received analyte concentration data to obtain analyte concentration data indicative of the analyte concentration in the host absent the noise signal component.

6. The system of claim 5, wherein the processor is further adapted to capture details of the noise signal component by reducing a sampling period during which the analyte concentration data is measured or overclocking the sensor measurement circuitry.

7. The system of claim 1, further comprising a guard band having a same voltage differential as that existing between at least two electrodes of the analyte sensor to compensate for artifact-induced current flow across the voltage differential.

8. The system of claim 1, further comprising a processor adapted to directly adjust the analyte concentration data by a predetermined adjustment amount based upon one or more factors causing the fluctuation.

* * * * *